United States Patent [19]

Cover et al.

[11] Patent Number: 5,721,349
[45] Date of Patent: Feb. 24, 1998

[54] VACUOLATING TOXIN-DEFICIENT H. PYLORI

[75] Inventors: Timothy L. Cover; Martin J. Blaser, both of Nashville, Tenn.

[73] Assignee: Vanderbilt University, Nashville, Tenn.

[21] Appl. No.: 200,232

[22] Filed: Feb. 23, 1994

Related U.S. Application Data

[63] Continuation-in-part of Ser. No. 841,644, Feb. 26, 1992, abandoned.

[51] Int. Cl.$^6$ .......... A61K 39/106; C12N 15/31; C12N 1/20; C07H 21/04
[52] U.S. Cl. .......... 536/22.1; 536/23.7; 536/24.3; 536/24.32; 435/250.3; 435/320.1; 435/69.1; 435/69.3; 424/238.1
[58] Field of Search .............. 424/184.1, 185.1, 424/238.1; 435/69.3, 172.1, 69.1, 91.1, 91; 536/22.1, 23.7

[56] References Cited

U.S. PATENT DOCUMENTS 5,001,230  3/1991  Brown et al. .............. 536/27

FOREIGN PATENT DOCUMENTS 9318150  9/1993  Italy.
WO 94/04161  3/1994  WIPO.

OTHER PUBLICATIONS

Schmitt et al Molecular Microbiology 12:307–319, 1994.
Umata et al. "The Cytotoxic Action of Diphtheria Ioxin and Its Degradation in Intact Vero Cells are inhibited by Balifomycin A1, a Specific Inhibitor of Vacuolar–Type H+–ATPase" *J. Biol. Chem.*275(35):21940–21945, Dec. 1990.
Cover et al The Journ. of Biol. Chem. 267:10510–10515, 1992.
Suggs et al, PNAS 78:6613–6617,1981.
Young et al, PNAS 80:1194–1198, 1983.
Owen et al Eur. Journ. of Epidemiology 9:315–321 1993.
Wyle et al Eur. Journ of Gastroenterology & Hepatology 5:59–515, 1993.
Schmitt et al Molecular Microbiology 12:307–319, 1994.
Muniates et al Representative chapter 12.
Cover, T.L. and Blaser, M.J. Ann. Rev. Med. 43:135–145, 1992.
Crabtree et al. *The Lancet*338:332–335, 1991.
Cover et al. *Infec. and Immun.*58(3):603–610, 1990.
Figura et al. *J. Clin. Microbiol.*27(1):225–226, 1989.
Leunk et al. *J. Med. Microbiol.*26:93–99, 1988.

*Primary Examiner*—Hazel F. Sidberry
*Attorney, Agent, or Firm*—Needle & Rosenberg, P.C.

[57] ABSTRACT

An isolated nucleic acid encoding the *Helicobacter pylori* vacuolating toxin, consisting of the nucleotides 101 through 3964 of the nucleotide sequence defined in the Sequence Listing as SEQ ID NO:1 is provided. An isolated nucleic acid from *Helicobacter pylori* comprising the nucleotide sequence defined in the Sequence Listing as SEQ ID NO:3 is provided. Isolated nucleic acids that selectively hybridize with the nucleic acids of the invention are provided. Also provided is a genetically altered mutant strain of *H. pylori* that does not express a functional vacuolating toxin. Purified proteins encoded by the nucleic acids of the invention are provided. A composition comprising an immunogenic amount of a protein or mutant strain of the invention in a pharmaceutically acceptable carrier is provided. A method of immunizing a subject against infection by *H. pylori*, comprising administering to the subject an immunogenic composition of the invention is provided.

5 Claims, No Drawings ers or primers for detecting the presence of an organism
5,721,349

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 4042 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 101..3964

( x i ) SEQUENCE DESCRIPTION: SEQ ID NO:1:

```
TATTTATAGC  CTTAATCGTA  AATGCAACAG  AAATTTTCTA  GTTTAAAGTC  GCACCCTTTG           60

TGCAAAAAAT  TGTTTTACAA  GAAAAGAAGA  AAGGAAAGAA  ATG  GAA  ATA  CAA  CAA        115
                                                  Met  Glu  Ile  Gln  Gln
                                                   1                      5

ACA  CAC  CGC  AAA  ATC  AAT  CGC  CCT  CTG  GTT  TCT  CTT  GCT  TTA  GTA  GGA  163
Thr  His  Arg  Lys  Ile  Asn  Arg  Pro  Leu  Val  Ser  Leu  Ala  Leu  Val  Gly
                     10                      15                      20

GCA  TTG  GTC  AGC  ATC  ACA  CCG  CAA  CAA  AGT  CAT  GCC  GCC  TTT  TTT  ACA  211
Ala  Leu  Val  Ser  Ile  Thr  Pro  Gln  Gln  Ser  His  Ala  Ala  Phe  Phe  Thr
                 25                      30                      35
```

| | | | | | | | | | | | | | | | | |
|---|---|---|---|---|---|---|---|---|---|---|---|---|---|---|---|---|
| ACC | GTG | ATC | ATT | CCA | GCC | ATT | GTT | GGG | GGC | ATC | GCT | ACA | GGC | ACC | GCT | 259 |
| Thr | Val | Ile | Ile | Pro | Ala | Ile | Val | Gly | Gly | Ile | Ala | Thr | Gly | Thr | Ala | |
| | | 40 | | | | 45 | | | | | 50 | | | | | |
| GTA | GGA | ACG | GTC | TCA | GGG | CTT | CTT | GGC | TGG | GGG | CTC | AAA | CAA | GCC | GAA | 307 |
| Val | Gly | Thr | Val | Ser | Gly | Leu | Leu | Gly | Trp | Gly | Leu | Lys | Gln | Ala | Glu | |
| | 55 | | | | 60 | | | | | 65 | | | | | | |
| GAA | GCC | AAT | AAA | ACC | CCA | GAT | AAA | CCC | GAT | AAA | GTT | TGG | CGC | ATT | CAA | 355 |
| Glu | Ala | Asn | Lys | Thr | Pro | Asp | Lys | Pro | Asp | Lys | Val | Trp | Arg | Ile | Gln | |
| 70 | | | | 75 | | | | 80 | | | | | 85 | | | |
| GCA | GGA | AAA | GGC | TTT | AAT | GAA | TTC | CCT | AAC | AAG | GAA | TAC | GAC | TTA | TAC | 403 |
| Ala | Gly | Lys | Gly | Phe | Asn | Glu | Phe | Pro | Asn | Lys | Glu | Tyr | Asp | Leu | Tyr | |
| | | | | 90 | | | | | 95 | | | | | 100 | | |
| AAA | TCC | CTT | TTA | TCC | AGT | AAG | ATT | GAT | GGA | GGT | TGG | GAT | TGG | GGG | AAT | 451 |
| Lys | Ser | Leu | Leu | Ser | Ser | Lys | Ile | Asp | Gly | Gly | Trp | Asp | Trp | Gly | Asn | |
| | | | 105 | | | | | 110 | | | | | 115 | | | |
| GCC | GCT | ACG | CAT | TAT | TGG | ATC | AAA | GGC | GGG | CAA | TGG | AAT | AAG | CTT | GAA | 499 |
| Ala | Ala | Thr | His | Tyr | Trp | Ile | Lys | Gly | Gly | Gln | Trp | Asn | Lys | Leu | Glu | |
| | | 120 | | | | | 125 | | | | | 130 | | | | |
| GTG | GAT | ATG | AAA | GAC | GCT | GTA | GGG | ACT | TAT | AAA | CTC | TCA | GGG | CTA | AGG | 547 |
| Val | Asp | Met | Lys | Asp | Ala | Val | Gly | Thr | Tyr | Lys | Leu | Ser | Gly | Leu | Arg | |
| 135 | | | | | 140 | | | | | 145 | | | | | | |
| AAC | TTT | ACT | GGT | GGG | GAT | TTA | GAT | GTC | AAT | ATG | CAA | AAA | GCC | ACC | TTG | 595 |
| Asn | Phe | Thr | Gly | Gly | Asp | Leu | Asp | Val | Asn | Met | Gln | Lys | Ala | Thr | Leu | |
| 150 | | | | | 155 | | | | | 160 | | | | | 165 | |
| CGC | TTG | GGC | CAA | TTC | AAT | GGC | AAT | TCT | TTC | ACA | AGC | TAT | AAG | GAT | AGT | 643 |
| Arg | Leu | Gly | Gln | Phe | Asn | Gly | Asn | Ser | Phe | Thr | Ser | Tyr | Lys | Asp | Ser | |
| | | | | 170 | | | | | 175 | | | | | 180 | | |
| GCT | GAT | CGC | ACC | ACA | AGA | GTG | GAT | TTC | AAC | GCT | AAA | AAT | ATC | TTA | ATT | 691 |
| Ala | Asp | Arg | Thr | Thr | Arg | Val | Asp | Phe | Asn | Ala | Lys | Asn | Ile | Leu | Ile | |
| | | | 185 | | | | | 190 | | | | | 195 | | | |
| GAT | AAT | TTT | TTA | GAA | ATC | AAT | AAT | CGT | GTG | GGT | TCT | GGA | GCC | GGG | AGG | 739 |
| Asp | Asn | Phe | Leu | Glu | Ile | Asn | Asn | Arg | Val | Gly | Ser | Gly | Ala | Gly | Arg | |
| | | 200 | | | | | 205 | | | | | 210 | | | | |
| AAA | GCC | AGC | TCT | ACG | GTT | TTG | ACT | TTG | CAA | GCT | TCA | GAA | GGG | ATT | ACT | 787 |
| Lys | Ala | Ser | Ser | Thr | Val | Leu | Thr | Leu | Gln | Ala | Ser | Glu | Gly | Ile | Thr | |
| | 215 | | | | | 220 | | | | | 225 | | | | | |
| AGC | AGT | AAA | AAT | GCT | GAA | ATT | TCT | CTT | TAT | GAT | GGC | GCT | ACG | CTC | AAT | 835 |
| Ser | Ser | Lys | Asn | Ala | Glu | Ile | Ser | Leu | Tyr | Asp | Gly | Ala | Thr | Leu | Asn | |
| 230 | | | | | 235 | | | | | 240 | | | | | 245 | |
| TTG | GCT | TCA | AAC | AGC | GTT | AAA | TTA | AAT | GGC | AAT | GTG | TGG | ATG | GGC | CGT | 883 |
| Leu | Ala | Ser | Asn | Ser | Val | Lys | Leu | Asn | Gly | Asn | Val | Trp | Met | Gly | Arg | |
| | | | | 250 | | | | | 255 | | | | | 260 | | |
| TTG | CAA | TAC | GTG | GGA | GCG | TAT | TTG | GCC | CCT | TCA | TAC | AGC | ACG | ATA | AAC | 931 |
| Leu | Gln | Tyr | Val | Gly | Ala | Tyr | Leu | Ala | Pro | Ser | Tyr | Ser | Thr | Ile | Asn | |
| | | | 265 | | | | | 270 | | | | | 275 | | | |
| ACT | TCA | AAA | GTG | ACA | GGG | GAA | GTG | AAT | TTT | AAC | CAT | CTC | ACT | GTG | GGC | 979 |
| Thr | Ser | Lys | Val | Thr | Gly | Glu | Val | Asn | Phe | Asn | His | Leu | Thr | Val | Gly | |
| | | 280 | | | | | 285 | | | | | 290 | | | | |
| GAT | CAC | AAC | GCC | GCT | CAA | GCA | GGC | ATT | ATC | GCT | AGT | AAC | AAG | ACT | CAT | 1027 |
| Asp | His | Asn | Ala | Ala | Gln | Ala | Gly | Ile | Ile | Ala | Ser | Asn | Lys | Thr | His | |
| | 295 | | | | | 300 | | | | | 305 | | | | | |
| ATT | GGC | ACA | CTG | GAT | TTG | TGG | CAA | AGC | GCG | GGG | TTA | AAT | ATC | ATT | GCC | 1075 |
| Ile | Gly | Thr | Leu | Asp | Leu | Trp | Gln | Ser | Ala | Gly | Leu | Asn | Ile | Ile | Ala | |
| 310 | | | | | 315 | | | | | 320 | | | | | 325 | |
| CCT | CCC | GAA | GGT | GGC | TAC | AAG | GAT | AAA | CCT | AAT | AAT | ACC | CCT | TCT | CAA | 1123 |
| Pro | Pro | Glu | Gly | Gly | Tyr | Lys | Asp | Lys | Pro | Asn | Asn | Thr | Pro | Ser | Gln | |
| | | | | 330 | | | | | 335 | | | | | 340 | | |
| AGT | GGT | GCT | AAA | AAC | GAC | AAA | CAA | GAG | AGC | AGT | CAA | AAT | AAT | AGT | AAC | 1171 |
| Ser | Gly | Ala | Lys | Asn | Asp | Lys | Gln | Glu | Ser | Ser | Gln | Asn | Asn | Ser | Asn | |
| | | | 345 | | | | | 350 | | | | | 355 | | | |

-continued

| | | | | | | | | | | | | | | | | |
|---|---|---|---|---|---|---|---|---|---|---|---|---|---|---|---|---|
| ACT | CAG | GTC | ATT | AAC | CCA | CCC | AAT | AGC | ACG | CAA | AAA | ACA | GAA | GTT | CAA | 1219 |
| Thr | Gln | Val | Ile | Asn | Pro | Pro | Asn | Ser | Thr | Gln | Lys | Thr | Glu | Val | Gln | |
| | | 360 | | | | 365 | | | | | | 370 | | | | |
| CCC | ACG | CAA | GTC | ATT | GAT | GGG | CCT | TTT | GCG | GGT | GGC | AAA | GAC | ACG | GTT | 1267 |
| Pro | Thr | Gln | Val | Ile | Asp | Gly | Pro | Phe | Ala | Gly | Gly | Lys | Asp | Thr | Val | |
| 375 | | | | | 380 | | | | | | 385 | | | | | |
| GTC | AAT | ATT | GAT | CGC | ATC | AAC | ACT | AAA | GCC | GAT | GGC | ACG | ATT | AAA | GTG | 1315 |
| Val | Asn | Ile | Asp | Arg | Ile | Asn | Thr | Lys | Ala | Asp | Gly | Thr | Ile | Lys | Val | |
| 390 | | | | | 395 | | | | | 400 | | | | | 405 | |
| GGA | GGG | TTT | AAA | GCT | TCT | CTT | ACC | ACC | AAC | GCG | GCT | CAT | TTG | AAT | ATC | 1363 |
| Gly | Gly | Phe | Lys | Ala | Ser | Leu | Thr | Thr | Asn | Ala | Ala | His | Leu | Asn | Ile | |
| | | | | 410 | | | | | 415 | | | | | 420 | | |
| GGC | AAA | GGC | GGT | GTC | AAT | CTG | TCC | AAT | CAA | GCG | AGC | GGG | CGC | ACC | CTT | 1411 |
| Gly | Lys | Gly | Gly | Val | Asn | Leu | Ser | Asn | Gln | Ala | Ser | Gly | Arg | Thr | Leu | |
| | | | 425 | | | | | 430 | | | | | 435 | | | |
| TTA | GTG | GAA | AAT | CTA | ACC | GGG | AAT | ATC | ACC | GTT | GAT | GGG | CCT | TTA | AGA | 1459 |
| Leu | Val | Glu | Asn | Leu | Thr | Gly | Asn | Ile | Thr | Val | Asp | Gly | Pro | Leu | Arg | |
| | | | 440 | | | | | 445 | | | | | 450 | | | |
| GTG | AAT | AAT | CAA | GTG | GGT | GGC | TAT | GCT | TTG | GCA | GGA | TCA | AGC | GCG | AAT | 1507 |
| Val | Asn | Asn | Gln | Val | Gly | Gly | Tyr | Ala | Leu | Ala | Gly | Ser | Ser | Ala | Asn | |
| | 455 | | | | | 460 | | | | | 465 | | | | | |
| TTT | GAA | TTT | AAG | GCT | GGT | GTG | GAT | ACT | AAA | AAC | GGC | ACA | GCC | ACT | TTC | 1555 |
| Phe | Glu | Phe | Lys | Ala | Gly | Val | Asp | Thr | Lys | Asn | Gly | Thr | Ala | Thr | Phe | |
| 470 | | | | | 475 | | | | | 480 | | | | | 485 | |
| AAT | AAC | GAT | ATT | AGT | CTG | GGA | AGA | TTT | GTG | AAT | TTA | AAG | GTG | GAT | GCT | 1603 |
| Asn | Asn | Asp | Ile | Ser | Leu | Gly | Arg | Phe | Val | Asn | Leu | Lys | Val | Asp | Ala | |
| | | | | 490 | | | | | 495 | | | | | 500 | | |
| CAT | ACA | GCT | AAT | TTT | AAA | GGT | ATT | GAT | ACG | GGT | AAT | GGT | GGT | TTC | AAC | 1651 |
| His | Thr | Ala | Asn | Phe | Lys | Gly | Ile | Asp | Thr | Gly | Asn | Gly | Gly | Phe | Asn | |
| | | | 505 | | | | | 510 | | | | | 515 | | | |
| ACC | TTA | GAT | TTT | AGT | GGT | GTT | ACA | AAC | AAG | GTC | AAT | ATC | AAC | AAG | CTC | 1699 |
| Thr | Leu | Asp | Phe | Ser | Gly | Val | Thr | Asn | Lys | Val | Asn | Ile | Asn | Lys | Leu | |
| | | 520 | | | | | 525 | | | | | 530 | | | | |
| ATT | ACG | GCT | TCC | ACT | AAT | GTG | GCC | GTT | AAA | AAC | TTC | AAC | ATT | AAT | GAA | 1747 |
| Ile | Thr | Ala | Ser | Thr | Asn | Val | Ala | Val | Lys | Asn | Phe | Asn | Ile | Asn | Glu | |
| | 535 | | | | | 540 | | | | | 545 | | | | | |
| TTG | ATT | GTT | AAA | ACC | AAT | GGG | GTG | AGC | GTG | GGG | GAA | TAC | ACT | CAT | TTT | 1795 |
| Leu | Ile | Val | Lys | Thr | Asn | Gly | Val | Ser | Val | Gly | Glu | Tyr | Thr | His | Phe | |
| 550 | | | | | 555 | | | | | 560 | | | | | 565 | |
| AGC | GAA | GAT | ATA | GGC | AGT | CAA | TCG | CGC | ATC | AAT | ACC | GTG | CGT | TTG | GAA | 1843 |
| Ser | Glu | Asp | Ile | Gly | Ser | Gln | Ser | Arg | Ile | Asn | Thr | Val | Arg | Leu | Glu | |
| | | | | 570 | | | | | 575 | | | | | 580 | | |
| ACT | GGC | ACT | AGG | TCA | ATC | TTT | TCT | GGG | GGT | GTC | AAA | TTT | AAA | AGC | GGC | 1891 |
| Thr | Gly | Thr | Arg | Ser | Ile | Phe | Ser | Gly | Gly | Val | Lys | Phe | Lys | Ser | Gly | |
| | | | 585 | | | | | 590 | | | | | 595 | | | |
| GAA | AAA | TTG | GTT | ATA | GAT | GAG | TTT | TAC | TAT | AGC | CCT | TGG | AAT | TAT | TTT | 1939 |
| Glu | Lys | Leu | Val | Ile | Asp | Glu | Phe | Tyr | Tyr | Ser | Pro | Trp | Asn | Tyr | Phe | |
| | | 600 | | | | | 605 | | | | | 610 | | | | |
| GAC | GCT | AGG | AAT | ATT | AAA | AAT | GTT | GAA | ATC | ACC | AGA | AAA | TTC | GCT | TCT | 1987 |
| Asp | Ala | Arg | Asn | Ile | Lys | Asn | Val | Glu | Ile | Thr | Arg | Lys | Phe | Ala | Ser | |
| | 615 | | | | | 620 | | | | | 625 | | | | | |
| TCA | ACC | CCA | GAA | AAC | CCT | TGG | GGC | ACA | TCA | AAA | CTC | ATG | TTT | AAT | AAT | 2035 |
| Ser | Thr | Pro | Glu | Asn | Pro | Trp | Gly | Thr | Ser | Lys | Leu | Met | Phe | Asn | Asn | |
| 630 | | | | | 635 | | | | | 640 | | | | | 645 | |
| CTA | ACC | CTG | GGT | CAA | AAT | GCG | GTC | ATG | GAC | TAT | AGT | CAA | TTT | TCA | AAT | 2083 |
| Leu | Thr | Leu | Gly | Gln | Asn | Ala | Val | Met | Asp | Tyr | Ser | Gln | Phe | Ser | Asn | |
| | | | | 650 | | | | | 655 | | | | | 660 | | |
| TTA | ACC | ATT | CAG | GGG | GAT | TTT | ATC | AAC | AAT | CAA | GGC | ACT | ATC | AAC | TAT | 2131 |
| Leu | Thr | Ile | Gln | Gly | Asp | Phe | Ile | Asn | Asn | Gln | Gly | Thr | Ile | Asn | Tyr | |
| | | | 665 | | | | | 670 | | | | | 675 | | | |

| | | | | | | | | | | | | | | | | |
|---|---|---|---|---|---|---|---|---|---|---|---|---|---|---|---|---|
| CTG | GTC | CGA | GGC | GGG | AAA | GTG | GCA | ACC | TTA | AAT | GTA | GGC | AAT | GCA | GCA | 2179 |
| Leu | Val | Arg | Gly | Gly | Lys | Val | Ala | Thr | Leu | Asn | Val | Gly | Asn | Ala | Ala | |
| | | 680 | | | | 685 | | | | | 690 | | | | | |
| GCT | ATG | ATG | TTT | AAT | AAT | GAT | ATA | GAC | AGC | GCG | ACC | GGA | TTT | TAC | AAA | 2227 |
| Ala | Met | Met | Phe | Asn | Asn | Asp | Ile | Asp | Ser | Ala | Thr | Gly | Phe | Tyr | Lys | |
| | 695 | | | | | 700 | | | | | 705 | | | | | |
| CCG | CTC | ATC | AAG | ATT | AAC | AGC | GCT | CAA | GAT | CTC | ATT | AAA | AAT | ACA | GAG | 2275 |
| Pro | Leu | Ile | Lys | Ile | Asn | Ser | Ala | Gln | Asp | Leu | Ile | Lys | Asn | Thr | Glu | |
| 710 | | | | | 715 | | | | | 720 | | | | | 725 | |
| CAT | GTT | TTA | TTG | AAA | GCG | AAA | ATC | ATT | GGT | TAT | GGT | AAT | GTT | TCT | ACA | 2323 |
| His | Val | Leu | Leu | Lys | Ala | Lys | Ile | Ile | Gly | Tyr | Gly | Asn | Val | Ser | Thr | |
| | | | 730 | | | | | 735 | | | | | 740 | | | |
| GGT | ACC | AAT | GGC | ATT | AGT | AAT | GTT | AAT | CTA | GAA | GAG | CAA | TTC | AAA | GAG | 2371 |
| Gly | Thr | Asn | Gly | Ile | Ser | Asn | Val | Asn | Leu | Glu | Glu | Gln | Phe | Lys | Glu | |
| | | | 745 | | | | | 750 | | | | | 755 | | | |
| CGC | CTA | GCC | CTT | TAT | AAC | AAC | AAT | AAC | CGC | ATG | GAT | ACT | TGT | GTG | GTG | 2419 |
| Arg | Leu | Ala | Leu | Tyr | Asn | Asn | Asn | Asn | Arg | Met | Asp | Thr | Cys | Val | Val | |
| | | 760 | | | | | 765 | | | | | 770 | | | | |
| CGA | AAT | ACT | GAT | GAC | ATT | AAA | GCA | TGC | GGT | ATG | GCT | ATC | GGC | AAT | CAA | 2467 |
| Arg | Asn | Thr | Asp | Asp | Ile | Lys | Ala | Cys | Gly | Met | Ala | Ile | Gly | Asn | Gln | |
| | 775 | | | | | 780 | | | | | 785 | | | | | |
| AGC | ATG | GTG | AAC | AAC | CCT | GAC | AAT | TAC | AAG | TAT | CTT | ATC | GGT | AAA | GCA | 2515 |
| Ser | Met | Val | Asn | Asn | Pro | Asp | Asn | Tyr | Lys | Tyr | Leu | Ile | Gly | Lys | Ala | |
| 790 | | | | | 795 | | | | | 800 | | | | | 805 | |
| TGG | AAA | AAT | ATA | GGC | ATC | AGT | AAA | ACG | GCT | AAC | GGC | TCT | AAA | ATT | TCG | 2563 |
| Trp | Lys | Asn | Ile | Gly | Ile | Ser | Lys | Thr | Ala | Asn | Gly | Ser | Lys | Ile | Ser | |
| | | | | 810 | | | | | 815 | | | | | 820 | | |
| GTG | TAT | TAT | TTA | GGC | AAT | TCT | ACG | CCT | ACT | GAG | AAT | GGT | GGC | AAT | ACC | 2611 |
| Val | Tyr | Tyr | Leu | Gly | Asn | Ser | Thr | Pro | Thr | Glu | Asn | Gly | Gly | Asn | Thr | |
| | | | 825 | | | | | 830 | | | | | 835 | | | |
| ACA | AAT | TTA | CCC | ACA | AAC | ACC | ACT | AAC | AAT | GCG | CGT | TTC | GCT | AGC | TAC | 2659 |
| Thr | Asn | Leu | Pro | Thr | Asn | Thr | Thr | Asn | Asn | Ala | Arg | Phe | Ala | Ser | Tyr | |
| | | | 840 | | | | | 845 | | | | | 850 | | | |
| GCT | CTC | ATA | AAG | AAC | GCT | CCT | TTC | GCT | CAC | AGC | GCC | ACT | CCT | AAT | TTA | 2707 |
| Ala | Leu | Ile | Lys | Asn | Ala | Pro | Phe | Ala | His | Ser | Ala | Thr | Pro | Asn | Leu | |
| | 855 | | | | | 860 | | | | | 865 | | | | | |
| GTC | GCT | ATC | AAT | CAG | CAT | GAT | TTT | GGC | ACT | ATT | GAA | AGC | GTG | TTT | GAA | 2755 |
| Val | Ala | Ile | Asn | Gln | His | Asp | Phe | Gly | Thr | Ile | Glu | Ser | Val | Phe | Glu | |
| 870 | | | | | 875 | | | | | 880 | | | | | 885 | |
| TTG | GCT | AAC | CGC | TCT | AAA | GAT | ATT | GAC | ACG | CTT | TAT | GCT | AAC | TCA | GGC | 2803 |
| Leu | Ala | Asn | Arg | Ser | Lys | Asp | Ile | Asp | Thr | Leu | Tyr | Ala | Asn | Ser | Gly | |
| | | | | 890 | | | | | 895 | | | | | 900 | | |
| GCG | CAA | GGC | AGG | GAT | CTC | TTA | CAA | ACC | TTA | TTG | ATT | GAT | AGC | CAT | GAT | 2851 |
| Ala | Gln | Gly | Arg | Asp | Leu | Leu | Gln | Thr | Leu | Leu | Ile | Asp | Ser | His | Asp | |
| | | | 905 | | | | | 910 | | | | | 915 | | | |
| GCG | GGT | TAT | GCC | AGA | ACC | ATG | ATT | GAT | GCT | ACA | AGC | GCT | AAT | GAA | ATC | 2899 |
| Ala | Gly | Tyr | Ala | Arg | Thr | Met | Ile | Asp | Ala | Thr | Ser | Ala | Asn | Glu | Ile | |
| | | 920 | | | | | 925 | | | | | 930 | | | | |
| ACC | AAG | CAA | TTG | AAT | ACG | GCC | ACT | ACC | ACT | TTA | AAC | AAC | ATA | GCC | AGT | 2947 |
| Thr | Lys | Gln | Leu | Asn | Thr | Ala | Thr | Thr | Thr | Leu | Asn | Asn | Ile | Ala | Ser | |
| | 935 | | | | | 940 | | | | | 945 | | | | | |
| TTA | GAG | CAT | AAG | ACA | AGC | AGT | TTA | CAA | ACT | TTG | AGC | TTG | AGT | AAT | GCG | 2995 |
| Leu | Glu | His | Lys | Thr | Ser | Ser | Leu | Gln | Thr | Leu | Ser | Leu | Ser | Asn | Ala | |
| 950 | | | | | 955 | | | | | 960 | | | | | 965 | |
| ATG | ATT | TTA | AAT | TCT | CGT | TTA | GTC | AAT | CTC | TCT | AGA | AGG | CAC | ACC | AAC | 3043 |
| Met | Ile | Leu | Asn | Ser | Arg | Leu | Val | Asn | Leu | Ser | Arg | Arg | His | Thr | Asn | |
| | | | | 970 | | | | | 975 | | | | | 980 | | |
| AAT | ATT | GAC | TCG | TTC | GCT | AAG | CGC | TTA | CAA | GCT | TTA | AAA | GAC | CAA | AGA | 3091 |
| Asn | Ile | Asp | Ser | Phe | Ala | Lys | Arg | Leu | Gln | Ala | Leu | Lys | Asp | Gln | Arg | |
| | | | 985 | | | | | 990 | | | | | 995 | | | |

| | |
|---|---|
| TTC GCT TCT TTA GAA AGC GCG GCG GAA GTG TTG TAT CAA TTT GCC CCT<br>Phe Ala Ser Leu Glu Ser Ala Ala Glu Val Leu Tyr Gln Phe Ala Pro<br>1000                         1005                       1010 | 3139 |
| AAA TAT GAA AAA CCT ACC AAT GTT TGG GCT AAC GCT ATT GGA GGA GCG<br>Lys Tyr Glu Lys Pro Thr Asn Val Trp Ala Asn Ala Ile Gly Gly Ala<br>1015                       1020                      1025 | 3187 |
| AGC TTG AAT AAT GGC GGC AAC GCT TCA TTG TAT GGC ACA AGC GCG GGC<br>Ser Leu Asn Asn Gly Gly Asn Ala Ser Leu Tyr Gly Thr Ser Ala Gly<br>1030                       1035                       1040                 1045 | 3235 |
| GTA GAT GCT TAC CTT AAC GGA CAA GTG GAA GCC ATT GTG GGA GGG TTT<br>Val Asp Ala Tyr Leu Asn Gly Gln Val Glu Ala Ile Val Gly Gly Phe<br>                    1050                       1055                      1060 | 3283 |
| GGA AGC TAT GGT TAT AGC TCT TTT AAT AAT CAA GCG AAC TCT CTT AAC<br>Gly Ser Tyr Gly Tyr Ser Ser Phe Asn Asn Gln Ala Asn Ser Leu Asn<br>                1065                       1070                      1075 | 3331 |
| TCT GGA GCC AAT AAC ACT AAT TTT GGC GTG TAT AGC CGT ATC TTT GCT<br>Ser Gly Ala Asn Asn Thr Asn Phe Gly Val Tyr Ser Arg Ile Phe Ala<br>                1080                       1085                      1090 | 3379 |
| AAC CAG CAT GAA TTT GAT TTT GAA GCT CAA GGG GCG CTA GGG AGT GAT<br>Asn Gln His Glu Phe Asp Phe Glu Ala Gln Gly Ala Leu Gly Ser Asp<br>1095                       1100                       1105 | 3427 |
| CAA TCA AGC TTG AAT TTC AAA AGC GCT CTA CTG CGA GAT TTG AAT CAA<br>Gln Ser Ser Leu Asn Phe Lys Ser Ala Leu Leu Arg Asp Leu Asn Gln<br>1110                       1115                       1120                      1125 | 3475 |
| AGC TAT AAT TAC TTA GCC TAT AGC GCT GCA ACA AGA GCG AGC TAT GGT<br>Ser Tyr Asn Tyr Leu Ala Tyr Ser Ala Ala Thr Arg Ala Ser Tyr Gly<br>                1130                       1135                      1140 | 3523 |
| TAT GAC TTT GCG TTT TTC AGG AAC GCT TTG GTG TTA AAA CCA AGT GTG<br>Tyr Asp Phe Ala Phe Phe Arg Asn Ala Leu Val Leu Lys Pro Ser Val<br>                1145                       1150                      1155 | 3571 |
| GGC GTG AGC TAT AAC CAT TTA GGT TCA ACC AAC TTT AAA AGC AAC AGC<br>Gly Val Ser Tyr Asn His Leu Gly Ser Thr Asn Phe Lys Ser Asn Ser<br>                1160                       1165                      1170 | 3619 |
| ACT AAT AAA GTG GCT TTG AGT AAT GGC TCT AGC AGT CAG CAT CTA TTC<br>Thr Asn Lys Val Ala Leu Ser Asn Gly Ser Ser Ser Gln His Leu Phe<br>1175                       1180                       1185 | 3667 |
| AAC GCT AGC GCT AAT GTG GAA GCG CGC TAT TAT TAT GGG GAC ACT TCA<br>Asn Ala Ser Ala Asn Val Glu Ala Arg Tyr Tyr Tyr Gly Asp Thr Ser<br>1190                       1195                       1200                      1205 | 3715 |
| TAC TTC TAT ATG AAC GCT GGA GTT TTA CAA GAA TTT GCT AAC TTT GGT<br>Tyr Phe Tyr Met Asn Ala Gly Val Leu Gln Glu Phe Ala Asn Phe Gly<br>                1210                       1215                      1220 | 3763 |
| TCT AGC AAT GCG GTA TCT TTA AAC ACC TTT AAA GTG AAT GCT ACT CGC<br>Ser Ser Asn Ala Val Ser Leu Asn Thr Phe Lys Val Asn Ala Thr Arg<br>                1225                       1230                      1235 | 3811 |
| AAC CCT TTA AAT ACC CAT GCC AGA GTG ATG ATG GGT GGG GAA TTA AAA<br>Asn Pro Leu Asn Thr His Ala Arg Val Met Met Gly Gly Glu Leu Lys<br>                1240                       1245                      1250 | 3859 |
| TTA GCT AAA GAA GTG TTT TTG AAT TTG GGC GTT GTT TAT TTG CAC AAT<br>Leu Ala Lys Glu Val Phe Leu Asn Leu Gly Val Val Tyr Leu His Asn<br>1255                       1260                       1265 | 3907 |
| TTG ATT TCC AAT ATA GGC CAT TTC GCT TCC AAT TTA GGA ATG AGG TAT<br>Leu Ile Ser Asn Ile Gly His Phe Ala Ser Asn Leu Gly Met Arg Tyr<br>1270                       1275                       1280                      1285 | 3955 |
| AGT TTC TAATACCATT CTAAACCCA TGCTCAAAGC ATGGGTTGA AATCTTACAA<br>Ser Phe | 4011 |
| AACATTAACC CCTACAACGC ATACACGACA A | 4042 |

( 2 ) INFORMATION FOR SEQ ID NO:2:

( i ) SEQUENCE CHARACTERISTICS:
    ( A ) LENGTH: 1287 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Glu Ile Gln Gln Thr His Arg Lys Ile Asn Arg Pro Leu Val Ser
 1               5                  10                  15
Leu Ala Leu Val Gly Ala Leu Val Ser Ile Thr Pro Gln Gln Ser His
            20                  25                  30
Ala Ala Phe Phe Thr Thr Val Ile Ile Pro Ala Ile Val Gly Gly Ile
        35                  40                  45
Ala Thr Gly Thr Ala Val Gly Thr Val Ser Gly Leu Leu Gly Trp Gly
    50                  55                  60
Leu Lys Gln Ala Glu Glu Ala Asn Lys Thr Pro Asp Lys Pro Asp Lys
65                  70                  75                  80
Val Trp Arg Ile Gln Ala Gly Lys Gly Phe Asn Glu Phe Pro Asn Lys
                85                  90                  95
Glu Tyr Asp Leu Tyr Lys Ser Leu Leu Ser Ser Lys Ile Asp Gly Gly
            100                 105                 110
Trp Asp Trp Gly Asn Ala Ala Thr His Tyr Trp Ile Lys Gly Gly Gln
        115                 120                 125
Trp Asn Lys Leu Glu Val Asp Met Lys Asp Ala Val Gly Thr Tyr Lys
    130                 135                 140
Leu Ser Gly Leu Arg Asn Phe Thr Gly Gly Asp Leu Asp Val Asn Met
145                 150                 155                 160
Gln Lys Ala Thr Leu Arg Leu Gly Gln Phe Asn Gly Asn Ser Phe Thr
                165                 170                 175
Ser Tyr Lys Asp Ser Ala Asp Arg Thr Thr Arg Val Asp Phe Asn Ala
            180                 185                 190
Lys Asn Ile Leu Ile Asp Asn Phe Leu Glu Ile Asn Asn Arg Val Gly
        195                 200                 205
Ser Gly Ala Gly Arg Lys Ala Ser Ser Thr Val Leu Thr Leu Gln Ala
    210                 215                 220
Ser Glu Gly Ile Thr Ser Ser Lys Asn Ala Glu Ile Ser Leu Tyr Asp
225                 230                 235                 240
Gly Ala Thr Leu Asn Leu Ala Ser Asn Ser Val Lys Leu Asn Gly Asn
                245                 250                 255
Val Trp Met Gly Arg Leu Gln Tyr Val Gly Ala Tyr Leu Ala Pro Ser
            260                 265                 270
Tyr Ser Thr Ile Asn Thr Ser Lys Val Thr Gly Glu Val Asn Phe Asn
        275                 280                 285
His Leu Thr Val Gly Asp His Asn Ala Ala Gln Ala Gly Ile Ile Ala
    290                 295                 300
Ser Asn Lys Thr His Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                325                 330                 335
Asn Thr Pro Ser Gln Ser Gly Ala Lys Asn Asp Lys Gln Glu Ser Ser
            340                 345                 350
Gln Asn Asn Ser Asn Thr Gln Val Ile Asn Pro Pro Asn Ser Thr Gln
        355                 360                 365
Lys Thr Glu Val Gln Pro Thr Gln Val Ile Asp Gly Pro Phe Ala Gly
    370                 375                 380
```

-continued

```
Gly Lys Asp Thr Val Val Asn Ile Asp Arg Ile Asn Thr Lys Ala Asp
385                 390             395                 400

Gly Thr Ile Lys Val Gly Gly Phe Lys Ala Ser Leu Thr Thr Asn Ala
            405             410                 415

Ala His Leu Asn Ile Gly Lys Gly Val Asn Leu Ser Asn Gln Ala
            420             425                 430

Ser Gly Arg Thr Leu Leu Val Glu Asn Leu Thr Gly Asn Ile Thr Val
        435             440                 445

Asp Gly Pro Leu Arg Val Asn Asn Gln Val Gly Gly Tyr Ala Leu Ala
    450                 455                 460

Gly Ser Ser Ala Asn Phe Glu Phe Lys Ala Gly Val Asp Thr Lys Asn
465                 470             475                 480

Gly Thr Ala Thr Phe Asn Asn Asp Ile Ser Leu Gly Arg Phe Val Asn
                485             490                 495

Leu Lys Val Asp Ala His Thr Ala Asn Phe Lys Gly Ile Asp Thr Gly
            500             505                 510

Asn Gly Gly Phe Asn Thr Leu Asp Phe Ser Gly Val Thr Asn Lys Val
        515             520                 525

Asn Ile Asn Lys Leu Ile Thr Ala Ser Thr Asn Val Ala Val Lys Asn
530                 535                 540

Phe Asn Ile Asn Glu Leu Ile Val Lys Thr Asn Gly Val Ser Val Gly
545                 550             555                 560

Glu Tyr Thr His Phe Ser Glu Asp Ile Gly Ser Gln Ser Arg Ile Asn
                565             570                 575

Thr Val Arg Leu Glu Thr Gly Thr Arg Ser Ile Phe Ser Gly Gly Val
            580             585                 590

Lys Phe Lys Ser Gly Glu Lys Leu Val Ile Asp Glu Phe Tyr Tyr Ser
        595             600             605

Pro Trp Asn Tyr Phe Asp Ala Arg Asn Ile Lys Asn Val Glu Ile Thr
    610                 615                 620

Arg Lys Phe Ala Ser Ser Thr Pro Glu Asn Pro Trp Gly Thr Ser Lys
625                 630             635                 640

Leu Met Phe Asn Asn Leu Thr Leu Gly Gln Asn Ala Val Met Asp Tyr
            645             650                 655

Ser Gln Phe Ser Asn Leu Thr Ile Gln Gly Asp Phe Ile Asn Asn Gln
        660             665                 670

Gly Thr Ile Asn Tyr Leu Val Arg Gly Gly Lys Val Ala Thr Leu Asn
        675             680                 685

Val Gly Asn Ala Ala Ala Met Met Phe Asn Asn Asp Ile Asp Ser Ala
    690                 695                 700

Thr Gly Phe Tyr Lys Pro Leu Ile Lys Ile Asn Ser Ala Gln Asp Leu
705                 710             715                 720

Ile Lys Asn Thr Glu His Val Leu Leu Lys Ala Lys Ile Ile Gly Tyr
            725             730                 735

Gly Asn Val Ser Thr Gly Thr Asn Gly Ile Ser Asn Val Asn Leu Glu
        740             745                 750

Glu Gln Phe Lys Glu Arg Leu Ala Leu Tyr Asn Asn Asn Arg Met
        755             760                 765

Asp Thr Cys Val Val Arg Asn Thr Asp Asp Ile Lys Ala Cys Gly Met
    770                 775             780

Ala Ile Gly Asn Gln Ser Met Val Asn Asn Pro Asp Asn Tyr Lys Tyr
785                 790             795                 800

Leu Ile Gly Lys Ala Trp Lys Asn Ile Gly Ile Ser Lys Thr Ala Asn
```

|     |     |     |     |     |     |     |     |     | 805 |     |     |     |     | 810 |     |     |     |     | 815 |     |
| --- | --- | --- | --- | --- | --- | --- | --- | --- | --- | --- | --- | --- | --- | --- | --- | --- | --- | --- | --- | --- |

Gly Ser Lys Ile Ser Val Tyr Tyr Leu Gly Asn Ser Thr Pro Thr Glu
            820                     825               830

Asn Gly Gly Asn Thr Thr Asn Leu Pro Thr Asn Thr Thr Asn Asn Ala
        835                 840                 845

Arg Phe Ala Ser Tyr Ala Leu Ile Lys Asn Ala Pro Phe Ala His Ser
    850                 855                 860

Ala Thr Pro Asn Leu Val Ala Ile Asn Gln His Asp Phe Gly Thr Ile
865                 870                 875                     880

Glu Ser Val Phe Glu Leu Ala Asn Arg Ser Lys Asp Ile Asp Thr Leu
                885                 890                 895

Tyr Ala Asn Ser Gly Ala Gln Gly Arg Asp Leu Leu Gln Thr Leu Leu
            900                 905                 910

Ile Asp Ser His Asp Ala Gly Tyr Ala Arg Thr Met Ile Asp Ala Thr
            915                 920                 925

Ser Ala Asn Glu Ile Thr Lys Gln Leu Asn Thr Ala Thr Thr Thr Leu
        930                 935                 940

Asn Asn Ile Ala Ser Leu Glu His Lys Thr Ser Ser Leu Gln Thr Leu
945                 950                 955                     960

Ser Leu Ser Asn Ala Met Ile Leu Asn Ser Arg Leu Val Asn Leu Ser
                965                 970                 975

Arg Arg His Thr Asn Asn Ile Asp Ser Phe Ala Lys Arg Leu Gln Ala
            980                 985                 990

Leu Lys Asp Gln Arg Phe Ala Ser Leu Glu Ser Ala Ala Glu Val Leu
        995                 1000                1005

Tyr Gln Phe Ala Pro Lys Tyr Glu Lys Pro Thr Asn Val Trp Ala Asn
    1010                1015                1020

Ala Ile Gly Gly Ala Ser Leu Asn Asn Gly Gly Asn Ala Ser Leu Tyr
1025                1030                1035                    1040

Gly Thr Ser Ala Gly Val Asp Ala Tyr Leu Asn Gly Gln Val Glu Ala
            1045                1050                1055

Ile Val Gly Gly Phe Gly Ser Tyr Gly Tyr Ser Ser Phe Asn Asn Gln
            1060                1065                1070

Ala Asn Ser Leu Asn Ser Gly Ala Asn Asn Thr Asn Phe Gly Val Tyr
        1075                1080                1085

Ser Arg Ile Phe Ala Asn Gln His Glu Phe Asp Phe Glu Ala Gln Gly
        1090                1095                1100

Ala Leu Gly Ser Asp Gln Ser Ser Leu Asn Phe Lys Ser Ala Leu Leu
1105                1110                1115                    1120

Arg Asp Leu Asn Gln Ser Tyr Asn Tyr Leu Ala Tyr Ser Ala Ala Thr
            1125                1130                1135

Arg Ala Ser Tyr Gly Tyr Asp Phe Ala Phe Phe Arg Asn Ala Leu Val
        1140                1145                1150

Leu Lys Pro Ser Val Gly Val Ser Tyr Asn His Leu Gly Ser Thr Asn
        1155                1160                1165

Phe Lys Ser Asn Ser Thr Asn Lys Val Ala Leu Ser Asn Gly Ser Ser
    1170                1175                1180

Ser Gln His Leu Phe Asn Ala Ser Ala Asn Val Glu Ala Arg Tyr Tyr
1185                1190                1195                    1200

Tyr Gly Asp Thr Ser Tyr Phe Tyr Met Asn Ala Gly Val Leu Gln Glu
            1205                1210                1215

Phe Ala Asn Phe Gly Ser Ser Asn Ala Val Ser Leu Asn Thr Phe Lys
    1220                1225                1230

```
Val  Asn  Ala  Thr  Arg  Asn  Pro  Leu  Asn  Thr  His  Ala  Arg  Val  Met  Met
          1235                     1240                    1245

Gly  Gly  Glu  Leu  Lys  Leu  Ala  Lys  Glu  Val  Phe  Leu  Asn  Leu  Gly  Val
          1250                     1255                    1260

Val  Tyr  Leu  His  Asn  Leu  Ile  Ser  Asn  Ile  Gly  His  Phe  Ala  Ser  Asn
1265                     1270                    1275                    1280

Leu  Gly  Met  Arg  Tyr  Ser  Phe
                    1285
```

( 2 ) INFORMATION FOR SEQ ID NO:3:

( i ) SEQUENCE CHARACTERISTICS:
        ( A ) LENGTH: 1541 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1541

( x i ) SEQUENCE DESCRIPTION: SEQ ID NO:3:

```
GGC  GTG  CTG  GAT  TTG  TGG  CAA  AGC  GCG  GGG  TTA  AGC  ATT  ATC  ACC  CCT     48
Gly  Val  Leu  Asp  Leu  Trp  Gln  Ser  Ala  Gly  Leu  Ser  Ile  Ile  Thr  Pro
1                   5                        10                      15

CCA  GAA  GGC  GGT  TAT  GAG  AGT  AAA  ACT  AAA  GAT  AAC  CCT  TCT  CAA  AAC     96
Pro  Glu  Gly  Gly  Tyr  Glu  Ser  Lys  Thr  Lys  Asp  Asn  Pro  Ser  Gln  Asn
               20                       25                      30

AGC  CCT  AAA  AAT  GAC  ACG  CAA  AAA  ACA  GAA  ATT  CAA  CCC  ACT  CAA  GTC    144
Ser  Pro  Lys  Asn  Asp  Thr  Gln  Lys  Thr  Glu  Ile  Gln  Pro  Thr  Gln  Val
          35                      40                      45

ATT  GAT  GGG  CCT  TTT  GCG  GGC  GGT  AAA  GAC  ACG  GTC  GTG  AAT  ATT  TTC    192
Ile  Asp  Gly  Pro  Phe  Ala  Gly  Gly  Lys  Asp  Thr  Val  Val  Asn  Ile  Phe
     50                      55                      60

CAC  TTA  AAC  ACT  AAA  GCC  GAT  GGC  ACG  CTT  AAA  GCG  GGA  GGG  TTT  AAA    240
His  Leu  Asn  Thr  Lys  Ala  Asp  Gly  Thr  Leu  Lys  Ala  Gly  Gly  Phe  Lys
65                      70                      75                      80

GCT  TCT  CTT  ACC  ACC  AAT  GCG  GCT  CAT  TTG  CAT  ATC  GGC  GAA  GGC  GGT    288
Ala  Ser  Leu  Thr  Thr  Asn  Ala  Ala  His  Leu  His  Ile  Gly  Glu  Gly  Gly
                    85                      90                      95

GTC  AAT  CTG  TCC  AAT  CAA  GCG  AGC  GGG  CGC  TCT  TTA  TTA  GTG  GAA  AAC    336
Val  Asn  Leu  Ser  Asn  Gln  Ala  Ser  Gly  Arg  Ser  Leu  Leu  Val  Glu  Asn
               100                     105                     110

CTA  ACC  GGG  AAT  ATC  ACC  GTT  GAG  GGG  ACT  TTA  AGA  GTG  AAT  AAT  CAA    384
Leu  Thr  Gly  Asn  Ile  Thr  Val  Glu  Gly  Thr  Leu  Arg  Val  Asn  Asn  Gln
          115                     120                     125

GTG  GGC  GGT  GCT  GCT  GTG  GCA  GGC  TCA  AGC  GCG  AAT  TTT  GAG  TTT  AAG    432
Val  Gly  Gly  Ala  Ala  Val  Ala  Gly  Ser  Ser  Ala  Asn  Phe  Glu  Phe  Lys
     130                     135                     140

GCT  GGC  GCT  GAT  ACC  AAC  AAC  GCC  ACA  GCC  ACT  TTT  AAT  AAC  GAT  ATC    480
Ala  Gly  Ala  Asp  Thr  Asn  Asn  Ala  Thr  Ala  Thr  Phe  Asn  Asn  Asp  Ile
145                     150                     155                     160

CAT  CTA  GGA  AAA  GCG  GTG  AAT  TTA  AGA  GTG  GAT  GCT  CAT  ACA  GCT  TAT    528
His  Leu  Gly  Lys  Ala  Val  Asn  Leu  Arg  Val  Asp  Ala  His  Thr  Ala  Tyr
                    165                     170                     175

TTT  AAT  GGC  AAT  ATT  TAT  CTG  GGA  AAA  TCC  ACG  AAT  TTA  AGA  GTG  AAT    576
Phe  Asn  Gly  Asn  Ile  Tyr  Leu  Gly  Lys  Ser  Thr  Asn  Leu  Arg  Val  Asn
               180                     185                     190

GGC  CAT  AGC  GCT  CAT  TTT  AAA  AAT  ATT  GAT  GCC  ACA  AAG  AGC  GAT  AAC    624
Gly  His  Ser  Ala  His  Phe  Lys  Asn  Ile  Asp  Ala  Thr  Lys  Ser  Asp  Asn
          195                     200                     205
```

| | | | | | | | | | | | | | | | | |
|---|---|---|---|---|---|---|---|---|---|---|---|---|---|---|---|---|
| GGG | CTA | AAC | ACT | AGC | GCT | TTG | GAT | TTT | AGT | GGC | GTT | ACA | GAT | AAA | GTC | 672 |
| Gly | Leu | Asn | Thr | Ser | Ala | Leu | Asp | Phe | Ser | Gly | Val | Thr | Asp | Lys | Val | |
| | 210 | | | | 215 | | | | | 220 | | | | | | |
| AAT | ATC | AAC | AAG | CTC | ACT | ACA | TCT | GCC | ACT | AAT | GTG | AAC | GTC | AAA | AAC | 720 |
| Asn | Ile | Asn | Lys | Leu | Thr | Thr | Ser | Ala | Thr | Asn | Val | Asn | Val | Lys | Asn | |
| 225 | | | | | 230 | | | | | 235 | | | | | 240 | |
| TTT | GAC | ATT | AAG | GAA | TTA | GTG | GTT | ACA | ACC | CGT | GTT | CAG | AGT | TTT | GGA | 768 |
| Phe | Asp | Ile | Lys | Glu | Leu | Val | Val | Thr | Thr | Arg | Val | Gln | Ser | Phe | Gly | |
| | | | | 245 | | | | | 250 | | | | | 255 | | |
| CAA | TAC | ACT | ATT | TTT | GGC | GAA | AAT | ATA | GGC | GAT | AAG | TCT | CGC | ATT | GGT | 816 |
| Gln | Tyr | Thr | Ile | Phe | Gly | Glu | Asn | Ile | Gly | Asp | Lys | Ser | Arg | Ile | Gly | |
| | | | 260 | | | | | 265 | | | | | 270 | | | |
| GTC | GTT | AGT | TTG | CAA | ACG | GGA | TAT | AGC | CCG | GCC | TAT | TCT | GGG | GGC | GTT | 864 |
| Val | Val | Ser | Leu | Gln | Thr | Gly | Tyr | Ser | Pro | Ala | Tyr | Ser | Gly | Gly | Val | |
| | | | 275 | | | | | 280 | | | | | 285 | | | |
| ACT | TTT | AAA | AGC | GGT | AAA | AAA | CTG | GTT | ATA | GAT | GAA | ATT | TAC | CAT | GCC | 912 |
| Thr | Phe | Lys | Ser | Gly | Lys | Lys | Leu | Val | Ile | Asp | Glu | Ile | Tyr | His | Ala | |
| | 290 | | | | | 295 | | | | | 300 | | | | | |
| CCT | TGG | AAT | TAT | TTT | GAC | GCT | AGG | AAT | GTT | ACC | GAT | GTT | GAA | ATC | AAC | 960 |
| Pro | Trp | Asn | Tyr | Phe | Asp | Ala | Arg | Asn | Val | Thr | Asp | Val | Glu | Ile | Asn | |
| 305 | | | | | 310 | | | | | 315 | | | | | 320 | |
| AAG | AGG | ATT | CTT | TTT | GGA | GCC | CCA | GGA | AAC | ATT | GCC | GGC | AAA | ACA | GGG | 1008 |
| Lys | Arg | Ile | Leu | Phe | Gly | Ala | Pro | Gly | Asn | Ile | Ala | Gly | Lys | Thr | Gly | |
| | | | | 325 | | | | | 330 | | | | | 335 | | |
| CTT | ATG | TTT | AAT | AAC | CTA | ACC | CTA | AAC | AGC | AAC | GCA | AGC | ATG | GAT | TAT | 1056 |
| Leu | Met | Phe | Asn | Asn | Leu | Thr | Leu | Asn | Ser | Asn | Ala | Ser | Met | Asp | Tyr | |
| | | | 340 | | | | | 345 | | | | | 350 | | | |
| GGT | AAG | GAT | TTA | GAC | TTA | ACC | ATT | CAA | GGG | CAT | TTC | ACT | AAC | AAT | CAA | 1104 |
| Gly | Lys | Asp | Leu | Asp | Leu | Thr | Ile | Gln | Gly | His | Phe | Thr | Asn | Asn | Gln | |
| | | 355 | | | | | 360 | | | | | 365 | | | | |
| GGC | ACG | ATG | AAT | CTT | TTT | GTC | CAA | GAT | GGG | CGT | GTA | GCG | ACC | TTA | AAT | 1152 |
| Gly | Thr | Met | Asn | Leu | Phe | Val | Gln | Asp | Gly | Arg | Val | Ala | Thr | Leu | Asn | |
| | 370 | | | | | 375 | | | | | 380 | | | | | |
| GCA | GGC | CAT | CAA | GCA | AGC | ATG | ATA | TTT | AAT | AAT | TTA | GTG | GAT | AGC | GCG | 1200 |
| Ala | Gly | His | Gln | Ala | Ser | Met | Ile | Phe | Asn | Asn | Leu | Val | Asp | Ser | Ala | |
| 385 | | | | | 390 | | | | | 395 | | | | | 400 | |
| ACT | GGG | TTT | TAC | AAA | CCA | CTC | ATT | AAG | ATC | AAT | AAC | GCT | CAA | AAT | CTC | 1248 |
| Thr | Gly | Phe | Tyr | Lys | Pro | Leu | Ile | Lys | Ile | Asn | Asn | Ala | Gln | Asn | Leu | |
| | | | | 405 | | | | | 410 | | | | | 415 | | |
| ACT | AAA | AAT | AAA | GAA | CAT | GTT | TTA | GTG | AAA | GGG | CGA | AAC | ATT | GAT | TAT | 1296 |
| Thr | Lys | Asn | Lys | Glu | His | Val | Leu | Val | Lys | Gly | Arg | Asn | Ile | Asp | Tyr | |
| | | | 420 | | | | | 425 | | | | | 430 | | | |
| AAT | TTA | GTG | GGA | GTG | CAA | GGC | GCT | AGT | TAT | GAC | AAT | ATT | TCT | GCA | AGC | 1344 |
| Asn | Leu | Val | Gly | Val | Gln | Gly | Ala | Ser | Tyr | Asp | Asn | Ile | Ser | Ala | Ser | |
| | | 435 | | | | | 440 | | | | | 445 | | | | |
| AAC | ACC | AAT | CTG | CAA | GAG | CAA | TTC | AAA | GAG | CGC | CTA | GCC | CTT | TAT | AAC | 1392 |
| Asn | Thr | Asn | Leu | Gln | Glu | Gln | Phe | Lys | Glu | Arg | Leu | Ala | Leu | Tyr | Asn | |
| | 450 | | | | | 455 | | | | | 460 | | | | | |
| AAC | AAC | AAC | CGC | ATG | GAT | ATT | TGT | GTG | GTG | CGA | AAA | GGC | AAT | ACC | GAT | 1440 |
| Asn | Asn | Asn | Arg | Met | Asp | Ile | Cys | Val | Val | Arg | Lys | Gly | Asn | Thr | Asp | |
| 465 | | | | | 470 | | | | | 475 | | | | | 480 | |
| GAC | ATT | AAA | GCA | TGC | GGG | ATG | GCT | ATC | GGC | AAT | CAA | AGC | ATG | GTG | AAT | 1488 |
| Asp | Ile | Lys | Ala | Cys | Gly | Met | Ala | Ile | Gly | Asn | Gln | Ser | Met | Val | Asn | |
| | | | | 485 | | | | 490 | | | | | 495 | | | |
| AAC | CCT | AAC | GAT | TAC | AAA | TAT | CTT | GAA | GGT | AAG | GCA | TGG | AAA | AAT | ACA | 1536 |
| Asn | Pro | Asn | Asp | Tyr | Lys | Tyr | Leu | Glu | Gly | Lys | Ala | Trp | Lys | Asn | Thr | |
| | | | 500 | | | | | 505 | | | | | 510 | | | |
| GGG | AT | | | | | | | | | | | | | | | 1541 |
| Gly | | | | | | | | | | | | | | | | |

5,721,349

37

-continued ( 2 ) INFORMATION FOR SEQ ID NO:4:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gly Val Leu Asp Leu Trp Gln Ser Ala Gly Leu Ser Ile Ile Thr Pro
 1               5                  10                  15
Pro Glu Gly Gly Tyr Glu Ser Lys Thr Lys Asp Asn Pro Ser Gln Asn
            20                  25                  30
Ser Pro Lys Asn Asp Thr Gln Lys Thr Glu Ile Gln Pro Thr Gln Val
        35                  40                  45
Ile Asp Gly Pro Phe Ala Gly Gly Lys Asp Thr Val Val Asn Ile Phe
    50                  55                  60
His Leu Asn Thr Lys Ala Asp Gly Thr Leu Lys Ala Gly Gly Phe Lys
65                  70                  75                  80
Ala Ser Leu Thr Thr Asn Ala Ala His Leu His Ile Gly Glu Gly Gly
                85                  90                  95
Val Asn Leu Ser Asn Gln Ala Ser Gly Arg Ser Leu Leu Val Glu Asn
            100                 105                 110
Leu Thr Gly Asn Ile Thr Val Glu Gly Thr Leu Arg Val Asn Asn Gln
        115                 120                 125
Val Gly Gly Ala Ala Val Ala Gly Ser Ser Ala Asn Phe Glu Phe Lys
    130                 135                 140
Ala Gly Ala Asp Thr Asn Asn Ala Thr Ala Thr Phe Asn Asn Asp Ile
145                 150                 155                 160
His Leu Gly Lys Ala Val Asn Leu Arg Val Asp Ala His Thr Ala Tyr
                165                 170                 175
Phe Asn Gly Asn Ile Tyr Leu Gly Lys Ser Thr Asn Leu Arg Val Asn
            180                 185                 190
Gly His Ser Ala His Phe Lys Asn Ile Asp Ala Thr Lys Ser Asp Asn
        195                 200                 205
Gly Leu Asn Thr Ser Ala Leu Asp Phe Ser Gly Val Thr Asp Lys Val
    210                 215                 220
Asn Ile Asn Lys Leu Thr Thr Ser Ala Thr Asn Val Asn Val Lys Asn
225                 230                 235                 240
Phe Asp Ile Lys Glu Leu Val Val Thr Thr Arg Val Gln Ser Phe Gly
                245                 250                 255
Gln Tyr Thr Ile Phe Gly Glu Asn Ile Gly Asp Lys Ser Arg Ile Gly
            260                 265                 270
Val Val Ser Leu Gln Thr Gly Tyr Ser Pro Ala Tyr Ser Gly Gly Val
    275                 280                 285
Thr Phe Lys Ser Gly Lys Lys Leu Val Ile Asp Glu Ile Tyr His Ala
290                 295                 300
Pro Trp Asn Tyr Phe Asp Ala Arg Asn Val Thr Asp Val Glu Ile Asn
305                 310                 315                 320
Lys Arg Ile Leu Phe Gly Ala Pro Gly Asn Ile Ala Gly Lys Thr Gly
                325                 330                 335
Leu Met Phe Asn Asn Leu Thr Leu Asn Ser Asn Ala Ser Met Asp Tyr
            340                 345                 350
Gly Lys Asp Leu Asp Leu Thr Ile Gln Gly His Phe Thr Asn Asn Gln
        355                 360                 365
```

-continued

Gly Thr Met Asn Leu Phe Val Gln Asp Gly Arg Val Ala Thr Leu Asn
370                     375                 380

Ala Gly His Gln Ala Ser Met Ile Phe Asn Asn Leu Val Asp Ser Ala
385                 390                 395                 400

Thr Gly Phe Tyr Lys Pro Leu Ile Lys Ile Asn Asn Ala Gln Asn Leu
                405             410                 415

Thr Lys Asn Lys Glu His Val Leu Val Lys Gly Arg Asn Ile Asp Tyr
            420                 425                 430

Asn Leu Val Gly Val Gln Gly Ala Ser Tyr Asp Asn Ile Ser Ala Ser
            435             440                 445

Asn Thr Asn Leu Gln Glu Gln Phe Lys Glu Arg Leu Ala Leu Tyr Asn
    450             455                 460

Asn Asn Asn Arg Met Asp Ile Cys Val Val Arg Lys Gly Asn Thr Asp
465             470                 475                 480

Asp Ile Lys Ala Cys Gly Met Ala Ile Gly Asn Gln Ser Met Val Asn
                485             490                 495

Asn Pro Asn Asp Tyr Lys Tyr Leu Glu Gly Lys Ala Trp Lys Asn Thr
            500             505                 510

Gly ( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AAGGCTGGTG TGGATAC                                                                17

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CKNGTDATYT CNACRTTYTT                                                             20

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GATTTGTGAA TTTAAAGGTG G                                                           21

( 2 ) INFORMATION FOR SEQ ID NO:8:

( i ) SEQUENCE CHARACTERISTICS:
        ( A ) LENGTH: 22 base pairs ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTCTATATCA TTATTAAACA TC 22

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TAGTAACAAG ACTCATAT 18

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGTTAGCCGT TTTACTG 17

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GTGAAAGCGA AAAACAAG 18

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AAGAGAAGCT TTAAACCCTC C 21

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ATGGAAATAC AACAAACACA                                                         20

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CTCCAGAACC CACACGATT                                                          19

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TACAAACCTT ATTGATTGAT AGCC                                                    24

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AAGCTTGATT GATCACTCC                                                          19

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TTYTTYACNA CNGTNATHAT                                                         20

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TTRTTDATYT CNARRAARTT RTC                                                     23

VACUOLATING TOXIN-DEFICIENT H. PYLORI

RELATED APPLICATION

This application is a continuation-in-part application of U.S. application Ser. No. 07/841,644, filed Feb. 26, 1992 now abandoned.

GOVERNMENT ACKNOWLEDGMENT

This work was supported in part by R29 DK45293-02 from the National Institutes of Health, the Medical Research Service of the Department of Veterans Affairs, and R01 CA58834 from the National Cancer Institute. The government has certain rights in the invention.

BACKGROUND OF THE INVENTION

1. Field of the Invention

This invention relates to a genetically engineered mutant strain of *H. pylori* that does not express a functional vacuolating toxin, an isolated nucleic acid encoding the *Helicobacter pylori* vacuolating toxin, nucleic acids that selectively hybridize with the vacuolating toxin encoding nucleic acid and methods of immunizing against and treating *H. pylori* infection.

2. Background Art

*Helicobacter pylori* is the major causative agent of chronic superficial gastritis in humans, and infection with this organism is an important etiologic factor in the pathogenesis of peptic ulcer disease and possibly gastric cancer (1–3). Although essentially all *H. pylori*-infected persons develop histologic gastritis (4), the majority of *H. pylori*-infected persons remain asymptomatic (4), whereas others develop serious complications of infection such as peptic ulceration or adenocarcinoma of the stomach (2,3). Individual *H. pylori* isolates demonstrate a high level of genotypic diversity (5,6), but nearly all phenotypic characteristics of the organism are conserved. At present, the only phenotypic characteristics known to differ among strains are production of a vacuolating cytotoxin (7,8) and the presence of a 128 kDa cytotoxin-associated protein encoded by cagA (8). Persons with peptic ulcer disease are infected with vacuolating cytotoxin-producing strains more frequently than patients with gastritis alone (11,12). Similarly, serologic responses to the 128 kDa cytotoxin-associated CagA protein are associated with the presence of peptic ulceration in *H. pylori*-infected persons (8,14). Thus, these two related phenotypes are important virulence determinants that can affect the clinical outcome of *H. pylori* infection.

The vacuolating cytotoxin is produced in vitro by approximately 50% of *H. pylori* strains (7,8), and is active upon a variety of cell types (7). The inventors have purified the vacuolating cytotoxin from *H. pylori* 60190, and demonstrated that it migrates as an 87 kDa protein under denaturing and reducing conditions (U.S. Ser. No. 07/841, 644). It was not possible to isolate or sequence the gene encoding the protein until the protein was purified. Thus, it has not been possible to express large quantities of the vacuolating toxin for use as a diagnostic reagent or in a vaccine.

SUMMARY OF THE INVENTION

The invention provides an isolated nucleic acid encoding the *Helicobacter pylori* vacuolating toxin, consisting of the nucleotides 101 through 3964 of the nucleotide sequence defined in the Sequence Listing as SEQ ID NO:1. This nucleic acid is an example of double-stranded sequence for the vacA coding region of *H. pylori* provided by the invention. An isolated nucleic acid from *Helicobacter pylori* comprising the nucleotide sequence defined in the Sequence Listing as SEQ ID NO:3 is provided. This nucleic acid can be a double-stranded sequence for a vacA (vacuolating toxin) gene of a naturally occurring *H. pylori* strain that does not produce functional vacuolating toxin (tox⁻ strain).

Isolated nucleic acids that selectively hybridize with the nucleic acids of the invention are provided. The selectively hybridizing nucleic acids can be used, for example, as probes or primers for detecting the presence of an organism that has the nucleic acid to which it hybridizes. Such nucleic acids can encode a polypeptide, and, can thereby be placed in a vector and host to produce the toxin, an antigenically similar toxin, an antigenic fragment or a fragment exhibiting toxin function.

The present invention also provides a genetically altered mutant strain of *H. pylori* that does not express a functional vacuolating toxin.

The invention provides purified proteins encoded by the nucleic acids of the invention. One example of a protein of the invention is a vacuolating toxin of *H. pylori* (SEQ ID NO:2), encoded by nucleotides 101 through 3964 of the nucleotide sequence of SEQ ID NO:1.

The invention provides a composition comprising an immunogenic amount of a protein, genetically altered strain or naturally occurring tox⁻ strain of the invention in a pharmaceutically acceptable carrier. The protein used in this composition can be a vacuolating toxin protein of the invention. A method of immunizing a subject against infection by *H. pylori*, comprising administering to the subject an immunogenic composition of the invention is provided.

DETAILED DESCRIPTION OF THE INVENTION

Nucleic acids

The invention provides an isolated nucleic acid encoding the *Helicobacter pylori* vacuolating toxin, consisting of the nucleotides 101 through 3964 of the nucleotide sequence defined in the Sequence Listing as SEQ ID NO:1. This nucleic acid is an example of double-stranded sequence for the vacA coding region of *H. pylori* provided by the invention. An "isolated" nucleic acid is one that is separated from other *H. pylori* genes.

Also provided is an isolated nucleic acid of *Helicobacter pylori*, consisting of the nucleotide sequence defined in the Sequence Listing as SEQ ID NO:1. Thus, the sequence includes a regulatory sequence for the vacA coding region of *H. pylori*. A Shine-Dalgarno sequence consisting of nucleotides 91–95 of the nucleotide sequence defined in the Sequence Listing as SEQ ID NO:1 is specifically provided. The invention also provides any nucleic acid which encodes the protein defined in SEQ ID NO:1.

An isolated nucleic acid from *Helicobacter pylori* comprising the nucleotide sequence defined in the Sequence Listing as SEQ ID NO:3 is provided. This nucleic acid can be a double-stranded sequence for a vacA (vacuolating toxin) gene of a naturally occurring *H. pylori* strain that does not produce functional vacuolating toxin (tox⁻ strain). The nucleic acid of SEQ ID NO: 3 is a double-stranded partial sequence of a vacuolating toxin gene of a tox⁻ strain provided by the invention. The nucleic acid includes part of an open reading frame. The remaining sequence can be readily determined using the cloning and sequencing methods provided in the specification.

Isolated nucleic acids that selectively hybridize with the nucleic acids of the invention are provided. The selectively hybridizing nucleic acids can be used, for example, as probes or primers for detecting the presence of an organism that has the nucleic acid to which it hybridizes. Such nucleic acids can encode a polypeptide, and, can thereby be placed in a vector and host to produce the toxin, a functionally similar toxin, an antigenic fragment or a fragment exhibiting toxin function.

"Stringent conditions" refers to the washing conditions used in a hybridization protocol. In general, the washing conditions should be as stringent as possible (i.e., a combination of temperature and salt concentration should be chosen so that the denaturation temperature of a hybridized sequence is approximately 5°–20° C. below the calculated $T_m$ of the hybrid under study). The temperature and salt conditions can be determined empirically in preliminary experiments in which samples of reference DNA immobilized on filters are hybridized to the probe or sequence of interest and then washed under conditions of different stringencies. For example, stringent conditions are exemplified by hybridization at 68° C. for 18 h in 6× SSC, followed by multiple washes with 0.1× or 0.5× SSC at 65° C.

An isolated nucleic acid that selectively hybridizes with the nucleic acid consisting of the nucleotides 101 through 3964 of the nucleotide sequence of SEQ ID NO:1, or the nucleic acid encoding the protein of SEQ ID NO:1, under stringent conditions and has at least 70% sequence complementarity with the segment of the sequence to which it hybridizes is provided. Thus, the nucleic acid can be used as a probe or primer for detecting the presence of an organism that has a gene encoding a functional vacuolating toxin.

An isolated nucleic acid that selectively hybridizes with the nucleic acid consisting of the nucleotide sequence of SEQ ID NO:1 or the nucleic acid encoding the protein of SEQ ID NO:1, under stringent conditions and has at least 70% sequence complementarity with the segment of the sequence to which it hybridizes is provided. This selectively hybridizing nucleic acid includes one or more of the regulatory sequences located upstream of the vacuolating toxin coding sequence.

An isolated nucleic acid that selectively hybridizes with the nucleic acid of SEQ ID NO: 3 under stringent conditions is also provided. Because the nucleic acid of SEQ ID NO:3 is part of an open reading frame, a selectively hybridizing nucleic acid can encode a polypeptide.

The selectively hybridizing nucleic acids of the invention can have at least 70%, 80%, 85%, 90%, 95%, 97%, 98% and 99% complementarity with the segment of the sequence to which it hybridizes. The nucleic acids can be at least 20, 50, 100, 150, 200, 300, 500, 750, 1000, 2000, 3000 or 4000 nucleotides in length. Thus, the nucleic acid can be an alternative coding sequence for the toxin, or can be used as a probe or primer for detecting the presence of a strain that has a gene encoding a functional vacuolating toxin or a tox⁻ strain. If used as primers, the invention provides compositions including at least two nucleic acids which selectively hybridize with different regions so as to amplify a desired region. Depending on the length of the probe or primer, it can range between 70% complementary bases and full complementarity and still hybridize under stringent conditions. For example, for the purpose of diagnosing the presence of a functional vacuolating toxin producing $H.$ $pylori$ strain, the degree of complementarity between the hybridizing nucleic acid (probe or primer) and the sequence to which it hybridizes ($H.$ $pylori$ DNA from a sample) should be at least enough to exclude hybridization with a naturally occurring tox⁻ strain or genetically altered strain of the present invention. Thus, a nucleic acid that selectively hybridizes with a functional toxin coding sequence will not selectively hybridize under stringent conditions with a nucleic acid for the tox⁻ strain, and vice versa. Alternatively, probes or primers can be chosen that will hybridize with both tox⁺ and tox⁻ vacA genes under stringent conditions. The invention provides examples of these nucleic acids of $H.$ $pylori,$ so that the degree of complementarity required to distinguish selectively hybridizing from nonselectively hybridizing nucleic acids under stringent conditions can be clearly determined for each nucleic acid. It should also be clear that a selectively hybridizing nucleic acid will not hybridize with nucleic acids encoding unrelated proteins or proteins from other species.

One skilled in the art can readily obtain the nucleic acids of the present invention with routine experimentation to synthesize a full gene as well as shorter nucleotide fragments. For example, techniques for obtaining nucleic acids such as those provided in the Sequence Listing are specifically provided in the application. Furthermore, additional methods are provided in the art that can be utilized without significant modification. Ferretti et al. (*Proc. Natl. Acad. Sci.* 82:599–603 (1986)) and Wosnick et al. (*Gene* 76:153–160 (1989)) show routine methods to synthesize a gene of known sequence. More specifically, Ferretti et al. teach the synthesis of a 1057 base pair synthetic bovine rhodopsin gene from synthetic oligonucleotides. The synthesized gene was faithful to the known sequence (first sentence, page 603), demonstrating the reliability of this method of gene synthesis. Additionally, Wosnick et al. teach the synthesis of a maize glutathione-transferase (GST) gene using an efficient, one-step annealing/ligation protocol. This technique also produced a complete synthetic gene with 100% fidelity, which demonstrates the routine nature of this protocol.

Proteins

The invention provides purified proteins encoded by the nucleic acids of the invention. One example of a protein of the invention is a vacuolating toxin of $H.$ $pylori$ (SEQ ID NO:2), encoded by nucleotides 101 through 3964 of the nucleotide sequence of SEQ ID NO:1.

A purified antigenic protein encoded by a nucleic acid that selectively hybridizes with the nucleic acid consisting of the nucleotides 101 through 3964 of the nucleotide sequence of SEQ ID NO:1under stringent conditions and has at least 70% complementarity with segment of the sequence to which it hybridizes is provided.

Also provided is an antigenic protein encoded by the nucleic acid comprising the nucleotide sequence defined in the Sequence Listing as SEQ. ID NO:3. This protein can be expressed in an $E.$ $coli$ expression system or other suitable system as described herein.

The antigenic-proteins encoded by the selectively hybridizing nucleic acids of the invention will be encoded by a nucleic acid that hybridizes to the nonsense strand of the double-stranded reference nucleic acid. As used in this context, "protein" includes polypeptides and peptides. Thus, protein encoded by the selectively hybridizing nucleic acid will not be an unrelated or irrelevant protein or fragment.

An antigenic fragment of a protein of the invention can be isolated from the whole antigen by chemical or mechanical disruption. The purified fragments thus obtained can be tested to determine their antigenicity and specificity by the methods taught herein. An antigenic fragment is typically at least about 8 consecutive amino acids derived from the protein's amino acid sequence and should be unique to a functional or nonfunctional vacuolating toxin of $H.$ $pylori.$ The antigenic fragments of the present proteins can be recombinant proteins obtained by cloning the selectively hybridizing nucleic acids encoding the fragments in an expression system capable of producing the antigenic fragments of the protein. The nucleic acids that encode an antigenic protein can be determined by placing the nucleic acid in a host and expressing the its product. The products can then be screened against polyclonal or monoclonal antibodies raised against the intact native protein or against antibodies (that specifically react with *H. pylori*) present in the blood of infected subjects.

Once the amino acid sequence of the antigenic protein is provided, it is also possible to synthesize, using standard peptide synthesis techniques, peptide fragments chosen to correspond to toxic or immunoreactive regions of the antigen and to modify these fragments by inclusion, deletion or modification of particular amino acids residues in the derived sequences. Thus, synthesis or purification of an extremely large number of peptides derived from the proteins is possible.

The amino acid sequences of the present proteins can contain an immunoreactive portion of antigenic protein attached to sequences designed to provide for some additional property, such as solubility. The antigenic proteins and fragments can include amino acid sequences in which one or more amino acids have been substituted with another amino acid to provide for some additional property, such as to remove/add amino acids capable of disulfide bonding, to increase its bio-longevity, alter enzymatic activity, or improve immunogenicity. In any case, the polypeptide must posses the relevant bioactive property, such as immunoreactivity, immunogenicity, toxicity etc.

Mutant Organism

The present invention also provides a genetically engineered mutant strain of *H. pylori* that does not express a functional vacuolating toxin. This mutant strain is distinguishable from the naturally occurring tox⁻ *H. pylori* strains, for example, by the presence of a nucleic acid not found in native *H. pylori*. In one example, the mutant *H. pylori* strain is obtained by making an insertion mutation in the coding sequence for the vacuolating toxin as described in the Examples. Since the present invention provides the nucleic acid encoding the toxin, other methods of mutating the coding sequence of the toxin can be used to obtain other mutant strains as contemplated herein. Examples of the mutant *H. pylori* strains of the present invention are designated 84–183:v1 and 60190:v1.

Additional mutants can be prepared, for example, by substitution mutation in the coding sequence for the vacuolating toxin or deleting a portion of the vacuolating toxin gene so as to render the gene non-functional or produced in such low amounts that the organism is non-infectious, non-toxic, less toxic or attenuated to a statistically significant degree. Furthermore, by providing the nucleotide sequence for the nucleic acid encoding the toxin, the present invention permits the making of specific point mutations having the desired effect. The deletion, insertion or substitution mutations can be made in either or both the regulatory or coding region to prevent transcription or to render the transcribed product nonfunctional. For example, the Shine Dalgarno sequence shown in SEQ ID NO:1can be disrupted so that translation of the toxin protein is prevented or reduced to a statistically significant degree.

One such approach to the construction of a deletion or insertion mutant is via the Donnenberg method (Donnenberg and Kaper *Infect. Immun.* 4310–4317, 1991). A deletion in the toxin gene is created by deleting a restriction fragment and religating the clone. This mutant is cloned into suicide vector pILL570. The sacB gene of *Bacillus subtilis* is also cloned into the suicide vector to provide a conditionally lethal phenotype. This construct is transformed into *H. pylori* by electroporation, and transformants selected by spectinomycin resistance. The merodiploid strain which contains the suicide vector and the mutated version of the toxin gene are exposed to sucrose to directly select for organisms that have undergone a second recombination, resulting in the loss of the vector. These and other well known methods of making mutations can be applied to the nucleic acids provided herein to obtain other desired mutations.

Vaccines

The invention provides a composition comprising an immunogenic amount of a protein of the invention in a pharmaceutically acceptable carrier. The protein used in this composition can be a vacuolating toxin protein of the invention. A method of immunizing a subject against infection by *H. pylori*, comprising administering to the subject an immunogenic composition of the invention is provided.

A composition comprising an immunogenic amount of an antigenic protein encoded by a selectively hybridizing nucleic acid of the invention in a pharmaceutically acceptable carrier is provided. The nucleic acids encoding these proteins will naturally be the nucleic acids that hybridize with the non-coding or antisense strands set forth in the Sequence Listing. A method of immunizing a subject against infection by *H. pylori*, comprising administering to the subject the composition is also provided.

A composition comprising an immunogenic amount of the antigenic protein encoded by the nucleic acid comprising the nucleotide sequence defined in the Sequence Listing as SEQ ID NO:3 can be in a pharmaceutically acceptable carrier. A method of immunizing a subject against infection by *H. pylori*, comprising administering to the subject the composition.

The antigenic proteins, naturally occurring tox⁻ or genetically altered mutant *H. pylori* of this invention can be used in the construction of a vaccine comprising an immunogenic amount of the antigen, tox⁻ or mutant and a pharmaceutically acceptable carrier. The vaccine can be the entire antigen, the antigen on an intact *H. pylori* (in the case of the tox⁻ strains), *E. coli* or other strain, or an epitope (fragment) specific to the antigen. The vaccine can also be potentially cross-reactive with antibodies to other antigens. A method of immunizing a subject against infection by *H. pylori*, comprising administering to the subject the an immunogenic amount of the genetically altered *H. pylori*, proteins or tox⁻ strain is provided.

Determining Immunogenicity

The purified proteins and polypeptide fragments of the invention can be tested to determine their immunogenicity and specificity. Briefly, various concentrations of a putative immunogen fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter, an animal so inoculated with the antigen can be exposed to the bacterium to test the potential vaccine effect of the specific immunogenic protein or fragment. The specificity of a putative immunogenic fragment can be ascertained by testing sera, other fluids or lymphocytes from the inoculated animal for cross reactivity with other closely related bacteria.

Once immunogenicity is established as described above, immunogenic amounts of the antigen can be determined using standard procedures. Briefly, various concentrations of a putative specific immunoreactive epitope are prepared, administered to an animal and the extent of immunological response (e.g., the production of antibodies) of an animal to each concentration is measured. The immunizing dosage can then be verified by challenging the animal with the bacterium and observing the protective effects of the various amounts of immunogen. Other examples of methods of immunizing animals against *H. pylori* infection are described in Czinn and Nedrud (*Infection and Immunity* 59(7):2359–2363, 1991) and Thomas et al. (*Acta Gastro-Enterologica Belgica*, Suppl. 58:54, 1993).

The pharmaceutically acceptable carrier in the vaccine of thevaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. For example, method of treating *H. pylori* infection, comprising administering to the subject the immunogenic amount of the genetically altered *H. pylori* of the invention is provided. Thus, the invention provides methods of preventing or treating *H. pylori* infection and the associated diseases by administering the vaccine to a subject.

Vectors and Hosts

The nucleic acids of the invention can be in a vector suitable for expressing the nucleic acid. The nucleic acid in a vector can be in a host suitable for expressing the nucleic acid.

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong vital promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted DNAs in mammalian cells (such as COS7).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Nucleic Acid Detection (Diagnosis) Methods

The presence of the vacuolating toxin, an *H. pylori* expressing a functional toxin, a naturally occurring tox⁻ *H. pylori* or the present genetically altered mutant can be determined by detecting the presence of a nucleic acid specific for the toxin, toxin fragment, tox⁻ or mutated toxin gene. The specificity of these sequences for the wild-type, tox⁻, and mutated genes can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the gene in question.

The nucleic acid specific for the *H. pylori* strain or protein of interest can be detected using the selectively hybridizing nucleic acids of the invention. More particularly, nucleic acid amplification techniques, such as polymerase chain reaction or ligase chain reaction are utilized. Alternatively, the nucleic acid is detected utilizing direct hybridization or by utilizing a restriction fragment length polymorphism. For example, the present invention provides a method of detecting the presence of *H. pylori*, expressing or not expressing functional vacuolating toxin, comprising utilizing PCR primers which hybridize only with nucleic acids specific for the present toxin related nucleic acids is provided. The presence of amplification indicates the presence of the nucleic acid encoding the antigen. In addition, ascertaining the presence of a nucleotide sequence associated with a restriction endonuclease cleavage site can be used for detection. In another embodiment a restriction fragment of a DNA sample can be sequenced directly using, for example, Sanger ddNTp sequencing or 7-deaza-2'-deoxyguanosine 5'-triphosphate and Taq polymerase and compared to the known unique sequence to detect *H. pylori* strains. In a further embodiment, the present invention provides a selective amplification method using the selectively hybridizing nucleic acids of the invention. In yet another embodiment the relevant sequences can be detected by directly hybridizing the unique sequence with a probe comprising a selectively hybridizing nucleic acid that has the requisite degree of sequence identity with the sequence to be detected. Furthermore, the nucleotide sequence could be amplified prior to hybridization by the methods described above.

The probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under stringency conditions such that fully complementary sequences or sequences with 70%, 80%, 90% or 95% hybridize. The areas that carry DNA sequences that hybridize to the labeled DNA probe become labeled themselves as a consequence of the reannealing reaction. The areas of the filter that exhibit such labeling may then be visualized, for example, by autoradiography. The stringency of hybridization is usually 5° C. to 20° C. below the Ti (the irreversible melting temperature of the hybrid formed between the probe and its target sequence) for the given chain length. For 50 to 200 mers the recommended hybridization temperature is about 68° C. at a washing salt concentration of 0.1× to 0.5× SSC (9). However, the washing temperatures are unique to the sequence under investigation and the purpose of the hybridization, and are optimized for each variant as further described herein.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic variation. Alternatively, it may be possible to prepare oligonucleotides that will only bind to altered DNA, so that PCR will only result in multiplication of the DNA if a mutation is present. Other techniques, such as 3SR, which utilize RNA polymerase to achieve high copy number, can also be used where appropriate.

In yet another method, PCR may be followed by restriction endonuclease digestion with subsequent analysis of the resultant products. Induced mutations or naturally occurring variable sequences can result in the gain or loss of specific restriction endonuclease site(s). The gain or loss of a restriction endonuclease recognition site facilitates the detection of the mutation using restriction fragment length polymorphism (RFLP) analysis or by detection of the presence or absence of a polymorphic restriction endonuclease site in a PCR product that spans the sequence of interest.

For RFLP analysis, DNA is obtained, for example from the blood, gastric specimen, saliva, dental plaque or other bodily fluids of the subject suspected of containing the toxin, or *H. pylori* expressing functional toxin isolated from subject, and from a subject infected with non-toxin-expressing *H. pylori*, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, native tox⁻, genetically altered toxin or functional toxin DNA is detected by determining the number of bands detected and comparing this number to the DNA from a different strain.

Single strand conformational analysis (SSCA) offers a relatively quick method of detecting sequence changes which may be appropriate in at least some instances.

In general, primers for PCR and LCR are usually about 20 bp in length and the preferable range is from 15-25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and a final extension step of 5 min.

The following examples are intended to illustrate, but not limit, the invention. While the protocols described are typical of those that might be used, other procedures known to those skilled in the art may be alternatively employed.

EXAMPLES

Bacterial strains and growth conditions.

*H. pylori* 60190 (ATCC 49503), from which the vacuolating cytotoxin was originally purified (15), was used to clone the gene for the vacuolating cytotoxin. *H. pylori* 84-183 (ATCC 53726) and 87-199 were well-characterized strains previously shown to produce the vacuolating cytotoxin (8,9,16), and strains Tx30a, 86-313, and 87-203 were wild-type strains that fail to produce detectable cytotoxin activity in vitro (7-9,16). Twenty-six additional clinical *H. pylori* isolates from humans, which have been described previously (9), were also used to assess the conservation of the cytotoxin gene. *H. pylori* isolates were cultured on trypticase soy agar plates containing 5% sheep blood in a microaerobic atmosphere generated by CampyPak-Plus (BBL, Cockeysville, Md.) at 37° C. for 48 h.

Determination of partial amino acid sequences of the vacuolating cytotoxin.

The 87 kDa vacuolating cytotoxin from *H. pylori* 60190 was purified from broth culture supernatant as described previously (15), electrophoresed on a 7% acrylamide gel, and electroblotted onto a ProBlott membrane (Applied Biosystems, Foster City, Calif.) (15). The 87 kDa protein was then digested with Arg-C protease, fragments were separated chromatographically, and the amino acid sequences of three fragments were determined at the Microsequencing Laboratory of Rockefeller University, New York, N.Y., as described by Fernandez et al. (17).

Genetic techniques and nucleotide sequence analysis.

To isolate chromosomal DNA, *H. pylori* cells were lysed in GES (60% guanidium thiocyanate-0.1M EDTA-0.5% Sarkosyl), and the DNA was purified by chloroform extraction and precipitation with isopropanol (18). *H. pylori* 60190 chromosomal DNA was either sheared by sonication or partially digested with AluI; genomic libraries then were constructed using λZapII (Stratagene, La Jolla, Calif.), as described previously (9). The library was screened by plaque hybridization (19), using probes radiolabelled by primer extension with random hexamers (United States Biochemical, Cleveland, Ohio). From purified reactive clones, pBluescript containing the cloned DNA inserts were excised by coinfection with R408 helper phage and subcloned in *E. coli* XL1-Blue. After plasmid purification, restriction enzyme cleavage maps were generated, and nucleotide sequences were determined on both strands by use of the dideoxy chain termination procedure (20). The final nucleotide sequence of vacA from strain 60190 was determined entirely from cloned genomic DNA rather than PCR fragments. Putative promoter and Shine-Dalgarno sequences were identified by comparison with consensus sequences (21). A search of databases for homologous proteins was accomplished using FastA and FastDB programs, as well as the BLAST network service of the National Center for Biotechnology Information.

Cloning of the vacuolating cytotoxin gene of *H. pylori* 60190.

Degenerate oligonucleotide primers [(5' TTYTTYAC-NACNGTNATHAT 3') (SEQ ID NO: 17) and (5' TTRTT-DATYTCNARRAARTTRTC 3') (SEQ ID NO:18)], constructed on the basis of reverse translations of the N-terminus of the purified 87 kDa protein and an experimentally determined peptide sequence (amino acids residues 35-41 and 198-205, respectively, SEQ ID NOs:1and 2), were used to PCR-amplify a 0.5 kb band from *H. pylori* 60190 DNA. This PCR product was excised from a 1% agarose gel, purified using a Qiaex gel extraction kit (Qiagen, Chatsworth, Calif.), and subcloned in *E. coli* Nova Blue cells using the pT7 Blue T-vector kit (Novagen, Madison, Wis.) to yield pCTB1. The nucleotide sequence of pCTB1 corresponded to bases 203-714 of SEQ ID NO:1.

Screening of the λZapII library with pCTB1 yielded two different reactive clones (pCTB2 and pCTB3). The sequence encoding the N-terminus of the cytotoxin was identified in pCTB2, and sequences encoding two experimentally determined peptide sequences were identified in pCTB3. A 0.4 kb product (pCTB4) then was PCR-amplified from *H. pylori* 60190 DNA using a primer selected from the downstream portion of pCTB3 (5' AAGGCTGGTGTGGATAC 3') (SEQ ID NO:5), and a degenerate primer (5' CKNGTDATYTC-NACRTTYTT 3') (SEQ ID NO:6) synthesized by reverse translation of an experimentally determined peptide sequence (amino acid residues 617-625, SEQ ID NO:2). Screening of the genomic library of *H. pylori* 60190 with pCTB4 as a probe resulted in the purification of pCTB5. Screening of the library with the downstream 0.2 kb XbaI fragment of pCTB5 resulted in the isolation of clone pCTB6 and pCTB7. Each of the clones was digested with restriction endonucleases, and nucleotide sequences of relevant portions of each clone were determined. Restriction sites are: EcoRI, HindIII, XbaI, BglII.

Compilation of the sequences of multiple clones revealed a 3864 bp ORF, initiated by an ATG codon at position 101 (SEQ ID NO:1), and terminated by a TAA codon at position 3964 (SEQ ID NO:1). An inverted repeat sequence capable of forming a stem-loop structure in the mRNA ($\Delta G=-13.2$ kcal) extended from nucleotides 3975-3999. The ORF encoded a protein of 1287 amino acid residues, and the calculated molecular mass of the deduced polypeptide was 138,955 daltons. The sequence that encoded the experimentally determined N-terminal amino acid sequence of the 87 kDa cytotoxin was preceded by a 33 amino acid leader sequence, which was characterized by a central hydrophobic area and an Ala-Ala signal peptidase I cleavage site. A potential ribosome binding site (AGGAA) ended 5 bp upstream of the open reading frame. A second ORF, proceeding in the same direction as vacA, was identified in pCTB2 upstream from vacA. The stop codon of this $\geq 567$ bp ORF was not followed by an inverted repeat sequence. Thus, the vacA ORF encoded a polypeptide considerably larger than the mature 87 kDa cytotoxin. In agreement with these findings, Western blotting of *H. pylori* whole cells with anti-87 kDa serum revealed faint immunoreactive 120-150 kDa bands that were absent from culture supernatant.

Analysis of the vacuolating cytotoxin gene product.

The translated amino acid sequence and nucleotide sequence of vacA and the upstream sequence were compared with sequences in the PIR and Swiss-Prot data bases. The strongest homology was between the $\geq 567$ bp ORF located upstream from vacA and cysteinyl-tRNA synthetase (cysS) from *E. coli* (40% and 44% identity in two 50 amino acid regions) (26,27). There were no proteins with significant homology to the vacA gene product. However, several proteins with related C-terminal motifs and similar C-terminal processing were identified. These included IgA proteases from *Haemophilus influenzae* (28) and *Neisseria gonorrhoeae* (29), *Serratia marcescens* serine protease (30–32), the 120 kDa surface-exposed protein of *Rickettsia rickettsii* (OmpB) (33,34), the 120 kDa surface-layer protein of *Rickettsia prowazekii* (35), and the AIDA-I adhesin of enteropathogenic *E. coli* (EPEC)(36). Each of these genes encodes a large protein that undergoes C-terminal cleavage of peptides 30–60 kDa in size (28–36). An alternating hydrophobic amino acid motif commencing with phenylalanine at C-terminal position 1 is present in each of these proteins. This C-terminal segment is commonly found in Gram-negative outer membrane proteins (37). These proteins are all characterized by low cysteine content (2 to 4 cysteines per protein), which is probably related to the need to minimize disulfide bond formation during membrane transport (38,39). However, in the translated VacA protein as well as in three related proteases, two cysteine residues are located only 7–11 amino acids apart. Replacement of paired cysteine residues with serines in *S. marcescens* protease is associated with decreased secretion of the enzyme (31). The corresponding cysteine residues also may play a role in secretion of the *H. pylori* vacA gene product.

Analysis of the nucleotide sequence of the vacA ORF suggests that vacA encodes a 139 kDa protoxin that has 3 regions: a 33 amino acid leader sequence, a mature cytotoxin domain (approximately 87 kDa), and a cleaved C-terminal domain (approximately 48 kDa). With the exception of a markedly hydrophobic region at the N-terminus, the mature 87 kDa protein (amino acids 34 to approximately 842) is predominantly hydrophilic, and contains 68% extended sequence (Robson conformation). In contrast to the experimentally determined isoelectric point of 6.1 (15), the predicted isoelectric point of the VacA 87 kDa domain is 9.1; this discrepancy may be attributable to post-translational modification of the protein. The cleaved C-terminal domain is predominantly hydrophilic, has 50% extended sequence, and a predicted isoelectric point of 8.8. In agreement with the experimentally determined amino acid content of the 87 kDa cytotoxin (15), the 87 kDa domain and C-terminal domain are both rich in asparagine (12%).

Construction of vacA-negative mutant *H. pylori* strains.

To determine whether the vacA gene is present in a single or multiple copy, genomic DNA from *H. pylori* 60190 was prepared and Southern hybridizations performed using the inserts in pCTB1 or pCTB4 as probes. Both probes hybridized to a single BglII fragment of approximately 7 kb (not shown). The pCTB4 insert hybridized to a single 1.7 kb HindIII fragment, and as predicted from mapping studies, the pCTB1 insert hybridized to two HindIII fragments. For DNA digested with five additional enzymes (SacI, EcoRV, EcoRI, BamHI, and KpnI), the probes hybridized with single fragments of ≧12 kb. These results suggest that only a single copy of vacA exists in strain 60190, and are consistent with the physical-genetic mapping studies of Bukanov and Berg, which used pCTB1 as a vacA probe (40).

The vacA gene was disrupted to test the hypothesis that this gene encodes the vacuolating cytotoxin. A 1.6 kb fragment encoding the first 1236 bp of the vacA ORF plus 393 bp of upstream sequence was PCR-amplified from *H. pylori* 60190 DNA, and subcloned in pT7Blue to create pCTB8. This plasmid was partially digested with EcoRI, and ligated with a *Campylobacter coli* kanamycin (km) resistance gene (22,23). Plasmid pILL 600 was used as a source of a *Campylobacter coli* kanamycin (km) resistance gene (22,23). More specifically, pCTB8 was PCR-amplified from *H. pylori* 60190 DNA, using primers [(5' GTGAAAGC-GAAAAACAAG 3') (SEQ ID NO:11) and (5' AAGAGAAGCTTTAAACCCTCC 3') (SEQ ID NO:12)]. The km cassette from pILL600 (22,23) was ligated into the unique EcoRI site of pCTB8 to create pCTB8:km.

We then sought to introduce pCTB8:km, which is unable to replicate in *H. pylori*, into *H. pylori* by electroporation. *H. pylori* 84–183 cells were electroporated with pCTB8:km, and kanamycin-resistant transformants were selected as described by Ferrero et al. (24). Natural transformation was accomplished by adding DNA isolated from the *H. pylori* mutant 84–183:v1 to strain 60190 in the exponential phase of growth. The cells were harvested after 30 minutes and incubated overnight at 37° C. on blood agar plates. These cells were replated on blood agar plates containing kanamycin (40 μg/ml) and kanamycin-resistant transformants were selected after 2–3 days of growth.

Electroporation of $10^9$ cfu of strain 84–183 with 500 ng of pCTB8:km DNA yielded 200–300 kanamycin-resistant transformants.

Southern and colony blot hybridization.

To determine whether vacA had been disrupted in the transformed strains by allelic exchange, DNA isolated from wild-type strain 84–183 and the kanamycin-resistant *H. pylori* mutant 84–183:v1 were digested with HindIII, and Southern hybridization was performed with either the kanamycin gene or pCTB8 as probes. After restriction endonuclease digestions of *H. pylori* chromosomal DNA, standardized amounts of the fragments were electrophoresed on a 0.7% agarose gel in 0.04M Tris acetate-2 mM EDTA buffer (pH 8.2). Transfer to nylon membranes, hybridization with radiolabeled probes, and washing were as described previously (9). Colony blot hybridization of *H. pylori* strains was performed as described previously (9); hybridization was at 68° C. for 18 h in 6× SSC, followed by washes with 0.5× SSC at 65° C.

DNA from the kanamycin-resistant transformant 84–183:v1 hybridized to the km probe, whereas DNA from the wild-type strain did not, which indicated that the km gene had been rescued from the non-replicating plasmid. DNA from both the wild-type and mutant strain hybridized with pCTB8, but 84–183:v1 contained a new 1.8 kb hybridizing fragment and had lost a 0.6 kb fragment. These data indicated that the vacA gene had been disrupted by insertion of the km cassette, and that the vector sequence had been lost via a double cross-over event.

Natural transformation then was used to generate a vacA mutant of *H. pylori* 60190. Chromosomal DNA (1 μg) from strain 84–183:v1 was incubated with 107 cells of strain 60190, and approximately 300 kanamycin-resistant transformants were obtained. Southern hybridization of chromosomal DNA from the mutant 60190:v1 showed the expected km insertion within vacA, resulting in allelic replacement.

Characterization of vacA-negative *Helicobacter pylori* mutants.

To determine whether disruption of the vacA gene abolished production of the 87 kDa protein, culture supernatants from the wild-type strains 84–183 and 60190 and two isogenic mutants 84–183:v1 and 60190:v1 were immunoblotted with anti-87 kDa serum (15). As expected, supernatants from both wild-type strains contained an immunoreactive 87 kDa band, whereas this band was absent from supernatants of the mutant strains. Concentrated culture supernatants from the two wild-type and two isogenic mutant strains were tested for vacuolating cytotoxin activity in a tissue culture assay.

Assessment of vacuolating cytotoxin activity.

H. pylori wild-type strains and mutants were cultured in Brucella broth containing 5% fetal bovine serum, and concentrated culture supernatants were prepared by ultrafiltration (8,16). HeLa cells were cultured in Eagle's modified minimal essential medium containing 10% fetal bovine serum and 10 mM ammonium chloride (8,16). Serial dilutions of the H. pylori supernatants, standardized by protein concentration, were incubated with HeLa cells for 18 h, and cell vacuolation then was quantitated by neutral red uptake assay, as described previously (16, 25). Supernatant from the naturally occurring tox⁻ strain Tx30a was tested as a control.

As expected, supernatant from the reference tox⁺ wild-type strain 60190 contained significantly greater cytotoxin activity than supernatant from tox⁺ wild-type strain 84–183, but no cytotoxin activity was detectable in culture supernatants from the two genetically altered mutant strains. Thus, insertional mutation of the vacA gene resulted in the absence of both 87 kDa protein and vacuolating cytotoxin production.

Conservation of the vacuolating cytotoxin gene.

To investigate whether vacA sequences are present in H. pylori strains expressing cytotoxin activity in vitro (tox⁺) as well as in wild-type strains that do not express cytotoxin activity (tox⁻), 15 tox⁺ and 17 tox⁻ strains were studied by colony hybridization with pCTB1 as a probe. Each of the H. pylori strains hybridized strongly, whereas there was no hybridization with E. coli XL1Blue.

Next, to study potential restriction fragment polymorphisms of the vacA gene, HindIII-digested genomic DNA from 3 tox⁺ (84–183, 60190, or 87–199) and 3 tox⁻ H. pylori strains (87–203, 86–313, or Tx30a) was prepared. Southern hybridization was performed with 3 different vacA probes (the insert in pCTB1, pCTB4, or the 0.7 XbaI fragment of pCTB5). Chromosomal DNA from tox⁺ H. pylori strains were digested with HindIII, and the restriction fragments were separated on a 0.7% gel. The DNA was then transferred to a nylon membrane and hybridized with the labelled vacA probe under high stringency conditions. Hybridized probes were stripped from the membrane with 0.1M sodium hydroxide at 70° C. for 30 minutes prior to blotting with each new probe. DNA fragments from each of the 6 strains hybridized with the pCTB1 probe, and marked restriction fragment length polymorphism was present. pCTB4 hybridized with a 1.7 kb fragment in 5 of the 6 strains, and a 0.7 kb fragment from one strain. Hybridization of pCTB4 to the 3 tox⁺ strains was considerably more intense than hybridization to the 3 tox⁻ strains. The third probe (0.7 kb XbaI fragment of pCTB5) hybridized to fragments from all 6 strains with equal intensity. These data indicated that vacA sequences are present in both tox⁺ and tox⁻ H. pylori strains, but suggested that there is sequence diversity among strains in the middle region of the vacA gene.

PCR amplification of vacA fragments from tox⁺ and tox⁻ strains.

To investigate further the vacA sequences present in both tox⁺ and tox⁻ H. pylori strains, PCR-amplify fragments from the three different regions of the gene was carried out. DNA from 3 tox⁺ H. pylori strains (84–183, 60190, 87–199) and 3 tox⁻ H. pylori strains (87–203, 86–313, and Tx30a) were used as templates for amplification of vacA gene fragments. PCR reactions were performed for 30 cycles. Conditions were identical for the three amplifications (temperatures 94°, 50°, and 72° C).

Primers #1 and #2 (5' ATGGAAATACAACAAACACA 3') (SEQ ID NO:13) and (5' CTCCAGAACCCACACGATT 3') (SEQ ID NO:14), selected from the region of vacA encoding the N-terminus of the cytotoxin, amplified a 0.6 kb fragment from each of the H. pylori strains tested. Similarly, primers #5 and #6 (5' TACAAACCTTATTGATTGAT-AGCC 3') (SEQ ID NO:15) and (5' AAGCTTGATTGAT-CACTCC 3') (SEQ ID NO:16), selected from the downstream portion of vacA, also amplified a 0.6 kb fragment from each of the strains tested. However, primers #3 and #4, selected from the middle of the vacA ORF [(5' GATTTGT-GAATTTAAAGGTGG 3') (SEQ ID NO:7) and (5' GTC-TATATCATTATTAAACATC 3') (SEQ ID NO:8)] amplified a 0.6 kb fragment only from H. pylori 60190, 84–183, and 86–313, under stringent conditions (50°). Under lower stringency annealing conditions (39° C.), primers #3 and #4 amplified the expected 0.6 kb fragment from 4 of the H. pylori strains tested, but not from 87–203 or Tx30a. These results are consistent with the Southern hybridization studies, which also suggested the presence of marked sequence variability in the mid-region of the vacA ORF.

Sequence analysis of the vacA gene from tox⁻ H. pylori 87–203.

To investigate further the potential sequence divergence in vacA genes, PCR-amplification from a tox⁻ strain a fragment of the vacA gene that included the region of putative variability was attempted. A 1.5 kb fragment was amplified from tox⁻ strain 87–203 using primers [(5' TAG-TAACAAGACTCATAT 3') (SEQ ID NO:9) and (5' CGT-TAGCCGTTTTACTG 3') (SEQ ID NO:10)], corresponding to bp 1012–1029 and 2533–2549 (SEQ ID NO:1).

Sequencing of the subcloned PCR product on both strands indicated the presence of a ≧1541 bp ORF (SEQ ID NO:3). The nucleotide sequence of this ORF was aligned with vacA from tox⁺ strain 60190, and there was 70.7% identity. A comparison between the two deduced amino acid sequences indicated that there was 64.8% identity and 78.2% amino acid homology. Thus, sequence analysis, Southern hybridizations, and PCR analysis all indicated that there are significant differences between the vacA sequences of tox⁺ and tox⁻ H. pylori strains.

The data presented here indicate that genetic sequences for the vacuolating cytotoxin are present in all H. pylori strains tested, including both tox⁺ and tox⁻ isolates.

Throughout this application various publications are referenced by numbers within parentheses. The disclosures of these publications in their entireties are hereby incorporated by reference into this application in order to more fully describe the state of the art to which this invention pertains. The full citations for these publications are as follows:

REFERENCES

1. Cover, T. L., and Blaser, M. J. (1992) Annu. Rev. Med. 3, 135–145
2. Correa, P. (1992) Cancer Res. 52, 6735–6740
3. Hentschel, E., Brandstatter, G., Dragosics, B., Hirschl, A. M., Nemec, H., Schutze, K., Taufer, M., and Wurzer, H. (1993) N. Engl. J. Med. 328, 308–312
4. Dooley, C. P., Cohen, H., Fitzgibbons, P. L., Bauer, M., Appleman, M. D., Perez-Perez, G. I., and Blaser, M. J. (1989) N. Engl. J. Med. 321, 1562–1566
5. Foxall, P. A., Hu, L-T., and Mobley, H. L. T. (1992) J. Clin. Microbiol. 30, 739–741
6. Akopyanz, N., Bukanov, N. O., Westblom, T. R., Kresovich, S., and Berg, D. E. (1992) Nuc. Acids Res. 20, 5137–5142
7. Leunk, R. D., Johnson, P. T., David, B. C., Kraft, W. G., and Morgan, D. R. (1988) J. Med. Microbiol. 26, 93–99
8. Cover, T. L., Dooley, C. P., and Blaser, M. J. (1990) Infect. Immun. 58, 603–610
9. Tummuru, M. K. R., Cover, T. L., and Blaser, M. J. (1993) Infect. Immun. 61, 1799–1809
10. Covacci, A., Censini, S., Bugnoli, M., Tetracca, R., Burroni, D., Macchia, G., Massone, A., Papini, E., Xiang, Z., Figura, N., and Rappuoli, R. (1993) Proc. Natl. Acad. Sci. U.S.A. 90, 5791–5795
11. Figura, N., Guglielmetti, P., Rossolini, A., Barberi, A., Cusi, G., Mussmanno, R. A., Russi, M., and Quaranta, S. (1989) J. Clin. Microbiol. 27, 225–226
12. Goosens, H., Glupczynski, Y., Burette, A., Lambert, J.-P., Vlaes, L., and Butzler, J.-P. (1992) Med. Microbiol. Lett. 1, 153–159
13. Tee, W., Lambert, J. R., Pegorer, M., Dwyer, B. (1993) Gastroenterology 104, A789
14. Crabtree, J. E., Taylor, J. D., Wyatt, J. I., Heatley, R. V., Shallcross, T. M., Tompkins, D. S., and Rathbone, B. J. (1991) Lancet 338, 332–335
15. Cover, T. L., Blaser, M. J. (1992) J. Biol. Chem. 267, 10570–10575
16. Cover, T. L., Cao, P., Lind, C. D., Tham, K. T., and Blaser, M. J. (1993) Infect. Immun. 61, 5008–5012
17. Fernandez, J., DeMott, M., Atherton, D., and Mische, S. M. (1992) Anal. Biochem. 201,255–264
18. Schleif, R. F., and Wensink, P. C. (1981) Practical methods in molecular biology (Springer, New York), p. 98
19. Manialts, T., Fritsch, E. F., and Sambrook, J. (1989) Molecular cloning: a laboratory manual. Cold Spring Harbor, N.Y.
20. Sanger, F., Nicklen, S., and Coulson, A. R. (1977) Proc. Natl. Acad. Sci. U.S.A. 71, 1342–1346
21. Hawley, D. K., and McClure, W. R. (1983) Nucleic Acids Res. 11, 2237–2255
22. Labigne-Roussel, A., Courcoux, P., and Tompkins, L. (1988) J. Bacteriol. 170, 1704–1708
23. Suerbaum, S., Josenhans, C., and Labigne, A. (1993) J. Bacteriol. 175, 3278–3288
24. Ferrero, R. L., Cussac, V., Courcoux, P., and Labigne, A. (1992) J. Bacteriol. 174, 4212–4217
25. Cover, T. L., Puryear, W., Perez-Perez, G. I., and Blaser, M. J. (1991) Infect. Immun. 59, 1264–1270
26. Avalos, J., Corrochano, L. M., and Brenner, S. (1991) FEBS Lett. 286, 176–180
27. Hou, Y.-M., Shiba, K., Motres, C., and Schimmel P. (1991) Proc. Natl. Acad. Sci. U.S.A. 88, 976–980
28. Poulsen, K., Brandt, J., Hjorth, J. P., Thogersen, H. C., and Kilian, M. (1989) Infect. Immun. 57, 3097–
29. Pohlner, J., Halter, R., Beyreuther, K., and Meyer, T. F. (1987) Nature (London) 325, 458–462
30. Yanagida, N., Uozumi, T., and Beppu, T. (1986) J. Bacteriol. 166, 937–944
31. Miyazaki, H., Yanagida, N., Horinouchi, S., and Beppu, T. (1989) J. Bacteriol. 171, 6566–6572
32. Shikata, S., Shimada, K., Kataoka, H., Horinouchi, S., and Beppu, T. (1992) J. Biochem. 111,627–632
33. Gilmore, R. D., Jr., Joste, N., and McDonald, G. A. (1989) Mol. Microbiol. 3, 1579–1586
34. Gilmore, R. D., Jr., Cieplak, W., Jr., Policastro, P. F., and Hackstadt, T. (1991) Mol. Microbiol. 5, 2361–2370
35. Carl, M., Dobson, M. E., Ching, W. -M., and Dasch, G. A. (1990) Proc. Natl. Acad. Sci. U.S.A. 87, 8237–8241
36. Benz, I, and Schmidt, M. A. (1992) Mol. Microbiol. 6, 1539–1546
37. Struyve, M., Moons, M., and Tommassen, J. (1991) J. Mol. Biol. 218, 141–148
38. Klauser, T., Pohlner, J., and Meyer, T. F. (1990) EMBO Journal 9, 1991–1999
39. Pollock, M. R., and Richmond, M. H. (1962) Nature 194, 446–449
40. Bukanov, N. O., and Berg, D. E. (1994) Molec. Microbiol. (in press)

---

What is claimed is:

1. An isolated nucleic acid from *Helicobacter pylori* consisting of the nucleotide sequence defined in the Sequence Listing as SEQ ID NO:3 and complements thereof.

2. The nucleic acid of claim 1 in a vector.

3. The nucleic acid of claim 2 in a host.

4. An isolated *Helicobacter pylori* toxin⁻ strain-specific fragment of at least 20 nucleotides of at least one strand of the nucleic acid of claim 1, and complements thereof.

5. An isolated nucleic acid of at least 20 nucleotides specific for a *Helicobacter pylori* toxin⁻ strain that hybridizes with the nucleic acid of SEQ ID NO:3 under stringent conditions of hybridization at 68° C. for 18 h in 6× SSC, followed by multiple washes with 0.1× to 0.5× SSC at 65° C., and has at least 90% complementarity with the sequence to which it hybridizes.

* * * * *